United States Patent [19]
Graybill et al.

[11] Patent Number: 6,127,191
[45] Date of Patent: Oct. 3, 2000

[54] AMINOBENZENEDICARBOXYLIC ACID-BASED COMBINATORIAL LIBRARIES

[75] Inventors: Todd L. Graybill, Pottstown; Zhengdong Wu, Exton; Nalin Subasinghe, West Chester; Cynthia L. Fedde, Warrington; Joseph M. Salvino, Schwenksville, all of Pa.

[73] Assignee: 3-Dimensional Pharmaceuticals, Inc., Exton, Pa.

[21] Appl. No.: 08/980,062

[22] Filed: Nov. 26, 1997

Related U.S. Application Data

[60] Provisional application No. 60/032,284, Dec. 3, 1996.

[51] Int. Cl.[7] .......................... C07C 69/76; C07C 63/04; C07C 211/00
[52] U.S. Cl. .............................. 436/518; 560/8; 562/493; 564/305; 435/DIG. 34; 435/DIG. 40
[58] Field of Search ................................ 562/493; 560/8; 564/305; 435/DIG. 34, DIG. 40; 436/518

[56] References Cited

U.S. PATENT DOCUMENTS

| | | | |
|---|---|---|---|
| 5,288,514 | 2/1994 | Ellman | 427/2 |
| 5,463,564 | 10/1995 | Agrafiotis et al. | 364/496 |
| 5,646,285 | 7/1997 | Baindur et al. | 546/298 |

FOREIGN PATENT DOCUMENTS

| | | |
|---|---|---|
| 0 372 486 | 6/1990 | European Pat. Off. . |
| WO 92/00091 | 1/1992 | WIPO . |
| WO 94/20467 | 9/1994 | WIPO . |
| WO 94/28028 | 12/1994 | WIPO . |
| WO 95/02566 | 1/1995 | WIPO . |
| WO 95/16712 | 6/1995 | WIPO . |
| WO 96/26918 | 9/1996 | WIPO . |
| WO 96/40201 | 12/1996 | WIPO . |
| WO 96/40732 | 12/1996 | WIPO . |

OTHER PUBLICATIONS

Bunin, B.A. and J.A. Ellman, "A General and Expedient Method for the Solid–Phase Synthesis of 1,4–Benzodiazepine Derivatives," *J. Am. Chem. Soc.* 114:10997–10998 (1992).

Dankwardt, S.M. et al., "Combinatorial synthesis of small–molecule libraries using 3–amino–5–hydroxybenzoic acid," *Mol. Diversity* 1:113–120 (1995).

DeWitt, S.H. et al., "[Diversomers]: An approach to non-peptide, nonoligomeric chemical diversity," *Proc. Natl. Acad. Sci. USA* 90:6909–6913 (1993).

Dower, W.J. and S.P.A. Fodor, "Chapter 28. The Search for Molecular Diversity (II): Recombinant and Synthetic Randomized Peptide Libraries," *Annual Reports in Medicinal Chemistry*, Bristol, J.A., ed., Academic Press, Inc., San Diego, CA, pp. 271–280 (1991).

Ecker, D.J. et al., "Rational screening of oligonucleotide combinatorial libraries for drug discovery," *Nucl. Acids Res.* 21(8):1853–1856 (1993).

Englebretsen, D. R. and D.R.K. Harding, "Solid phase peptide synthesis on hydrophilic supports," *Int. J. Peptide Protein Res.* 40:487–496 (1992).

Farrall, M.J. and J.M.J. Fréchet, "Bromination and Lithiation: Two Important Steps in the Functionalization of Polystyrene Resins," *J. Org. Chem.* 41(24):3877–3882 (1976).

Frank, R. and R. Döring, "Simultaneous Multiple Peptide Synthesis under Continuous Flow Conditions on Cellulose Paper Discs as Segmental Solid Supports," *Tetrahedron* 44(19):6031–6040 (1988).

Furka, A. et al., "General method for rapid synthesis of multicomponent peptide mixtures," *Int. J. Peptide Protein Res.* 37:487–493 (1991).

Gallop, M.A. et al., "Applications of Combinatorial Technologies to Drug Discovery. 1. Background and Peptide Combinatorial Libraries," *J. Med. Chem.* 37(9):1233–1251 (1994).

Geysen, H.M. et al, "Strategies for epitope analysis using peptide synthesis," *J. Immunol. Methods* 102:259–274 (1987).

Goff, D.A. and R.N. Zuckermann, "Solid–Phase Synthesis of Highly Substituted Peptoid 1(2H)–Isoquinolinones," *J. Org. Chem.* 605748–5749.

Gold, L. et al., "Diversity of Oligonucleotide Functions," *Annu. Rev. Biochem.* 64:763–797 (1995).

Gordon, D.W. and J. Steele, "Reductive Alkylation on a Solid Phase: Synthesis of a Piperazinedione Combinatorial Library," *Bioorg. & Med. Chem. Letters* 5(1):47–50 (1995).

Gordon, E.M. et al., "Applications of Combinatorial Technologies to Drug Discover. 2. Combinatorial Organic Synthesis, Library Screening Strategies, and Future Directions," *J. Med. Chem.* 37(10):1385–1401 (1994).

Han, H. et al., "Liquid–phase combinatorial synthesis," *Proc. Natl. Acad. Sci. USA* 92:6419–6423 (1995).

(List continued on next page.)

*Primary Examiner*—Bennett Celsa
*Assistant Examiner*—Joseph W. Ricigliano
*Attorney, Agent, or Firm*—Sterne, Kessler, Goldstein & Fox P.L.L.C.

[57] ABSTRACT

The present invention provides a library of compounds, each comprised of a common aminobenzenedicarboxylic acid core structure (scaffold) that serves as a template for synthesizing approximately $10^1$–$10^6$ compounds which are analogs of the scaffold. The library is employed to study ligand binding by biological receptors, such as enzymes, G-protein coupled receptors and membrane channels. For example, certain individual compounds within the library selectively bind and inhibit the action of trypsin-like serine proteases. The present invention also relates to combinatorial synthetic methods for making such libraries of compounds. Additionally, the present invention relates to novel scaffold-modified solid supports, particularly scaffold-modified polymer resins and methods for preparing said resins. Further, the present invention is directed to methods for screening a compound or plurality of compounds made according to the synthetic methods disclosed herein, which comprise using the compounds in suitable assays developed for detecting the compounds' utility as pharmaceutical agents.

6 Claims, 4 Drawing Sheets

OTHER PUBLICATIONS

Hartman, G.D. et al., "Non–Peptide Fibrinogen Receptor Antagonists. 1. Discovery and Design of Exosite Inhibitors," *J. Med. Chem.* 35:4640–4642 (1992).

Hermkens, P.H.H. et al., "Solid–Phase Organic reactions: a Review of the Recent Literature," *Tetrahedron* 52(*13*):4527–4554 (Mar. 1996).

Jung. G. and A.G. Beck–Sickinger, "Multiple Peptide Synthesis Methods and their Applications," *Angewandte Chemie* 31(*4*):367383 (1992).

Kaldor, S.W. et al., "Discovery of Antirhinoviral Leads by Screening a Combinatorial Library of Ureas Prepared Using Covalent Scavengers," *Bioorg. & Med. Chem. Letters* 6(*24*):3041–3044 (Dec. 1996).

Lam, K.S. et al., "A new type of synthetic peptide library for identifying ligand–binding activity," *Nature* 354:82–84 (1991).

Merrifield, R.B., "Solid Phase Peptide Synthesis. I. the Synthesis of a Tetrapeptide," *J. Amer. Chem. Soc.* 85:2149–2154 (1963).

Meutermans, W.D.F. and P.F. Alewood, "The Solid Phase Synthesis of Dihydro– and Tetrahydroisoquinolines," *Tetrahedron Letters* 36(*42*):7709–7712 (1995).

Moran, E.J. et al., "Novel Biopolymers for Drug Discovery," *Biopolymers* (*Peptide Sci.*) 37(*3*):213–219 (1995).

Murphy, M.M. et al., "Combinatorial Organic Synthesis of Highly Functionalized Pyrrolidines: Identification of a Potent Angiotensin Converting Enzyme Inhibitor from a Mercaptoacyl Proline Library," *J. Am. Chem. Soc.* 117:7029–7030 (1995).

Pinilla, C. et al., "A Review of the Utility of Soluble Peptide Combinatorial Libraries," *BioPolymers* (*Peptide Sci.*) 37(*3*):221–240 (1995).

Qian, Y. et al., "Design and Synthesis of Non–Peptide Ras CAAX Mimetics as Potent Farnesyltransferase Inhibitors," *J. Med. Chem.* 39:217–223 (Jan. 1996).

Rink, H., "Solid–Phase Synthesis of Protected Peptide Fragments Using a Trialkoxy–Diphenyl–Methylester Resin," *Tetrahedron Letters* 28(*33*):3787–3790 (1987).

Sieber, P., "A New Acid–Labile Anchor Group for the Solid–Phase Synthesis of C–Terminal Peptide Amides by the FMOC Method," *Tetrahedron Letters* 28(*19*):2107–2110 (1987).

Smith III, A.B. et al., "Design and Synthesis of Peptidomimetic Inhibitors of HIV–1 Protease and Renin. Evidence for Improved Transport," *J. Med. Chem.* 37(*2*):215–218 (1994).

Terrett, N.K. et al., "Combinatorial Synthesis—The Design of Compound Libraries and their Application to Drug Discovery," *Tetrahedron* 51(*30*):8135–8173 (1995).

Valerio, R.M. et al., "Multipin peptide synthesis at the micromole scale using 2–hydroxyethyl methacrylate grafted polyethylene supports," *Int. J. Peptide Protein Res.* 42:1–9 (1993).

Zuckermann, R.N. et al., "Discovery of Nanomolar Ligands for 7–Transmembrane G–Protein–Coupled Receptors from a Diverse N–(Substituted)glycine Peptoid Library," *J. Med. Chem.* 37:2678–2685 (1994).

Dialog 31, Derwent WPI English Language abstract for EP 0 372 486 (1990).

IIb/IIIa RECEPTOR ANTAGONISTS

FARNESYL TRANSFERASE INHIBITORS

THROMBIN INHIBITORS

AMINOBENZENEDICARBOXYLIC ACID-BASED COMBINATORIAL LIBRARIES

This application claims priority to provisional application Ser. No. 60/032,284, filed Dec. 3, 1996, now abandoned.

BACKGROUND OF THE INVENTION

1. Field of the Invention

The present invention relates generally to the generation of libraries of chemical entities having defined physical, chemical or bioactive properties. More specifically, the invention provides libraries of compounds that possess a common core structure (scaffold) having diverse moieties attached to the scaffold.

2. Related Art

Conventionally, new chemical entities with useful properties are generated by identifying a chemical compound (called a "lead compound") with some desirable property or activity, creating variants of the lead compound, and evaluating the property and activity of those variant compounds. Examples of chemical entities with useful properties include paints, finishes, plasticizers, surfactants, scents, flavorings, and bioactive compounds, but can also include chemical compounds with any other useful property that depends upon chemical structure, composition, or physical state. Chemical entities with desirable biological activities include drugs, herbicides, pesticides and veterinary products. There are a number of flaws with this conventional approach to lead generation, particularly as it pertains to the discovery of bioactive compounds.

Historically, and presently, most novel pharmaceutical leads are obtained by screening large numbers of chemical entities. Some of these chemical entities are natural products while others are from synthetic compound collections. Rapid developments in molecular biology have provided many new therapeutic targets against which leads can be developed. Researchers are utilizing their recently acquired rapid robotic, high-throughput biological screening capability to search for leads within existing compound libraries for these biological targets. However, there are certain drawbacks in searching for leads within historically-collected compound libraries and natural product mixtures. Historically-collected compound libraries of pharmaceutical companies provide limited chemical and structural diversity. Lead identification and optimization from natural product mixtures remains a tedious and expensive process. To expand the molecular diversity against which high throughput screening could be carried out for lead identification, large biological and synthetic peptide combinatorial libraries (Gallop, M. A. et al., *J. Med. Chem.* 37:1233–1251 (1994); Pinilla, C. et al., *Biopolymers (Pept. Sci)* 37:221–240 (1995); Jung, G. et al., *Chem., Int. Ed. Engl.* 31:367–383 (1992); Dower, W. J. et al., *Annu. Rep. Med. Chem.* 26:271–280 (1991)), peptidomimetic combinatorial libraries (Zuckermann, R. N. et al., *J. Med. Chem.* 37:2678–2685 (1994); Moran, E. J. et al., *Biopolymers (Pept. Sci.)* 37:213–219 (1995)) and oligonucleotide combinatorial libraries (Ecker, D. J. et al., *Nucleic Acids Res.* 21:1853–1856 (1993); Gold, L. et al., *Annu. Rev. Biochem.* 64:763–797 (1995)) have been generated. However leads obtained from these linear polymer libraries usually have poor oral activity and rapid in vivo clearance (Smith, A. B. et al., *J. Med. Chem.* 37:215–218 (1994)). Consequently, converting these leads into orally active pharmaceutically useful drugs has met with limited success.

To overcome these limitations, nonoligomeric, low molecular weight synthetic libraries containing thousands of compounds have been generated. Some of these libraries have been synthesized as combinatorial mixtures while others were generated as single molecules by rapid parallel synthesis. See, for example, a benzodiazepine library generated by solid phase synthesis, which contains inhibitors of pp60s-src tyrosine kinase and ligands that block an autoimmune DNA-antibody interaction implicated in systemic lupus erythematosus (Bunin, B. A. and Ellman, J. A., *J. Am. Chem. Soc.* 114:10997–10998 (1992)), a diketopiperazine library containing ligands for the neurokinin-2 receptor (Gordon, D. W. and Steele, J., *BioMed. Chem. Lett.* 5:47–50 (1995)), and a pyrrolidine library containing a highly potent angiotensin-converting enzyme inhibitor (Murphy, M. M. et al., *J. Am. Chem. Soc.* 117:7029–7030 (1995)). See also, small molecule libraries of isoquinolinones (Goff, D. A. and Zuckermann, R. N., *J. Org. Chem.* 60:5748–5749 (1995)), dihydro- and tetrahydroisoquinolines (Meutermans, W. D. F. and Alewood, P. F., *Tetrahedron Lett.* 36:7709–7712 (1995)), and hydantoins (DeWitt, S. H. et al., *Proc. Natl. Acad Sci. U.S.A.* 90:6909–6913 (1993)). Even though in many cases further chemical modification of leads obtained from these small molecular libraries may be necessary to convert them into pharmaceutically useful drugs, this would be a more tractable task than optimizing a peptide or an oligonucleotide lead.

Among the greatest challenges in drug discovery is the conversion of peptide lead molecules with intermediate potency into high potency, non-peptide compounds with pharmacological properties that are appropriate for use as drugs. Recent advances in this effort have been the discovery of nonpolar, nonpeptide surrogates for peptide residues that have many of the characteristics desirable in a drug: low molecular weight, limited hydrophilicity and few or no chiral centers. For example, direct substitution of the RGD epitope, Arg-Gly-Asp-Trp (FIG. 4, i) with structurally rigid aromatic residues has provided several potent antagonists of the IIb/IIIa receptor (FIG. 4, ii) (Hartman et al., *J. Med. Chem.* 35:4640–4642 (1992)) and (FIG. 4, iii) (Alig et al., European Patent Application EP 0372486, 1990). In another example, inhibitors of the Ras Farnesyl transferase have been discovered in which the three C-terminal residues of a Cys-Val-Ile-Met lead (FIG. 4, iv) (Qian et al. *J. Med. Chem.* 4:2579–2584 (1994)) are replaced with a substituted biphenyl system (FIG. 4, v) (Qian et al. *J. Med. Chem.* 39:217–223 (1996)). Finally, thrombin inhibitors have been developed in which the central residue of D-Phe-Pro-descarboxy-Arg (FIG. 4, vi) is replaced with rigid orcinol group (FIG. 4, vii) (Von Der Saal, W., WO 94/20467).

Even though small molecule compound libraries have been generated to date, there exists a vast array of unexplored structural and chemical diversity that can be harnessed and utilized in the drug discovery process. In order to achieve this goal, there remains an urgent need to expand the solid phase chemistry methods for the preparation of low molecular weight, non-peptide compound libraries.

Dankwardt et al., Combinatorial Synthesis of Small-Molecule Libraries Using 3-Amino-5-hydroxybenzoic Acid, *Molecular Diversity* (1996) discloses the formation of a library of small organic molecules. The method and library utilizes 3-amino-5-hydroxybenzoic acid as the underlying core structure. The hydroxy group in the 5-position has a major influence on the types of compounds that can ultimately be prepared in the resulting library.

PCT published application WO 95/02566 describes a multiple component combinatorial array synthesis of compounds that share a common core structure and have at least three components.

U.S. Pat. No. 5,288,514 describes a solid phase combinatorial synthesis of benzodiazepine compounds.

PCT published application WO 95/16712 describes the use of silane chemistry and linkers in combinatorial syntheses of non-peptide compounds. The compounds are screened as pharmaceutical agents by screening for G-protein coupled receptor binding, enzyme inhibition and ability to block channels through cell membranes.

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states. The methods and libraries of the present invention offer a convenient and efficient way of developing lead compounds for modulating the activity of proteases and other therapeutically-relevant enzymes or receptors.

SUMMARY OF THE INVENTION

The present invention provides a library of compounds, each comprised of a common aminobenzenedicarboxylic acid core structure (scaffold) that serves as a template for synthesizing a collection of about $10^1$ to about $10^6$ compounds. The library is employed to study ligand binding by biological receptors, such as enzymes, G-protein coupled receptors and membrane channels. Certain compounds within the library bind and inhibit the action of trypsin-like serine proteases, such as thrombin or factor Xa. The present invention also relates to synthetic methods for high-throughput preparation of such libraries of compounds. Additionally, the present invention relates to novel scaffold-modified solid supports, particularly scaffold-modified polymer resins and methods for preparing said resins.

Further, the present invention is directed to methods for screening a compound or plurality of compounds made according to the synthetic methods disclosed herein, which comprise using the compounds in suitable assays developed for detecting utility as pharmaceutical agents.

Further features and advantages of the present invention, as well as the structure and operation of various embodiments of the present invention, are described in detail below.

DETAILED DESCRIPTION OF THE PREFERRED EMBODIMENTS

Figure 1:
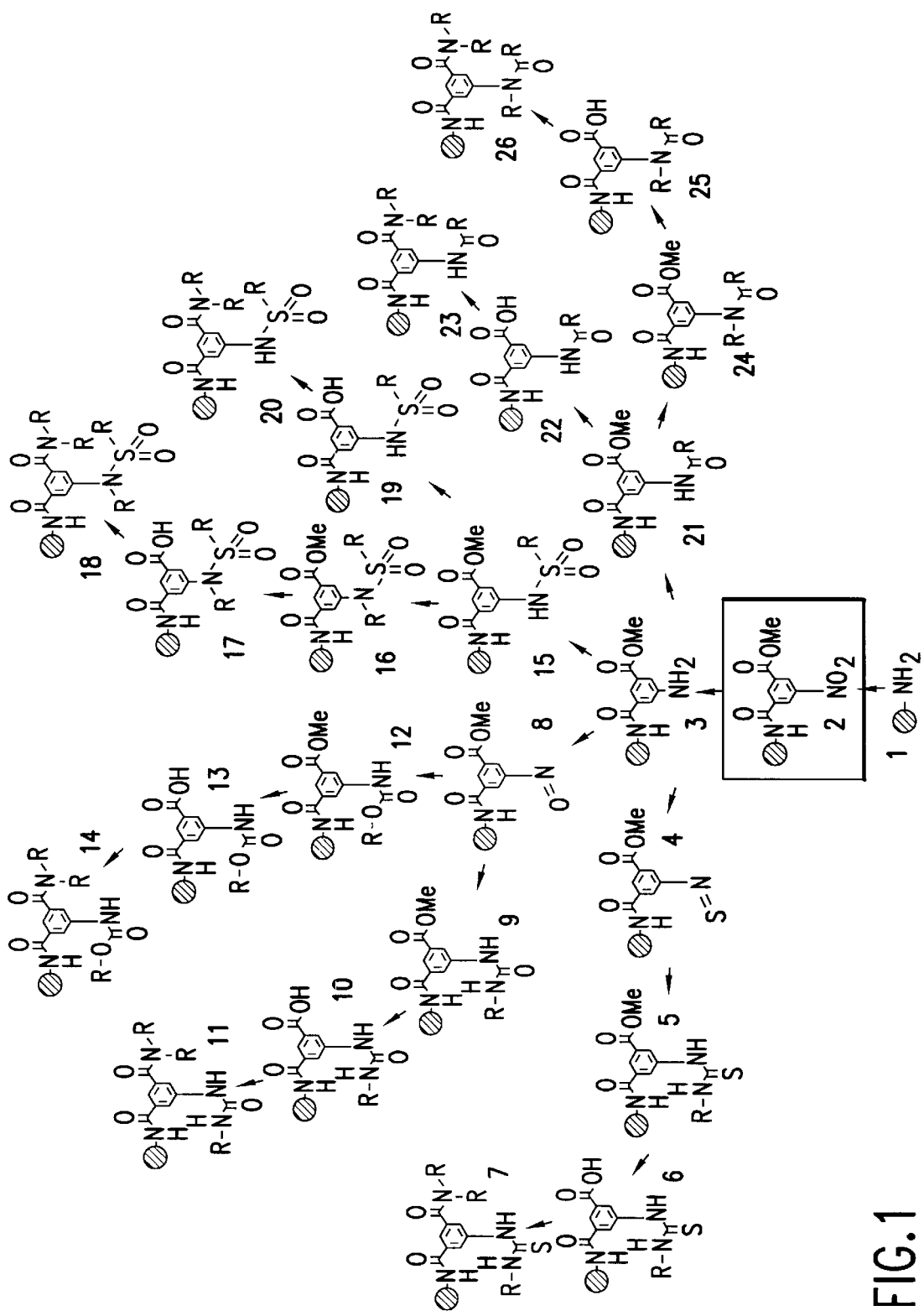
FIG. 1 depicts a synthesis tree that illustrates the diversity of chemical structure that can be achieved employing the methods and resins of the present invention. Schemes 4–11 herein describe the details for the synthesis of resins representing the trunk (resin 3) and branches (resins 7, 11, 14, 18, 20, 23 and 26) of this tree. In this particular tree, the nitro groups of resin 2 are reduced to amino groups and the resulting anilines are further reacted before the ester groups are hydrolyzed and coupled with amines.

The present invention employs nitro or amino substituted benzenedicarboxylic acids as rigid aromatic scaffolds that serve to replace or mimic peptide residues. The ready availability of these scaffolds and the methods described herein allow rapid preparation of spatially diverse molecules that as a collection rapidly define the pharmacophoric determinants (shape, volume, and electrostatic constraints) that are responsible for the binding of a small molecule to a given protease, enzyme, or receptor.

The compounds that are included in the libraries of the present invention are formed from two types of components: (1) a common aromatic scaffold or set of related scaffolds, and (2) at least two molecules having functional groups that react with suitably reactive functional groups present on the scaffold moiety. In this embodiment, the scaffold moiety is an appropriately functionalized phenyl ring that permits ready attachment of substituents in diverse spacial orientations.

A novel composition of matter has been developed for the solid phase synthesis of the libraries of the present invention. Thus, in one aspect of the present invention, is provided a composition of matter, comprising a solid support material having a plurality of pendant scaffold moieties covalently attached thereto, wherein said scaffold moieties have the formula:

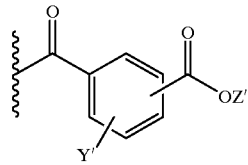

I where Y' is nitro or amino; Z' is hydrogen or a suitable carboxylic acid protecting group, including trialkylsilyl, alkyl, alkenyl, aryl or aralkyl, any of which is optionally substituted; and ⸳ represents the attachment point of the scaffold moiety to the solid support material, wherein said attachment is either directly to the solid support material or via a cleavable linker. In a preferred embodiment, the composition is formed by attaching a compound of the formula:

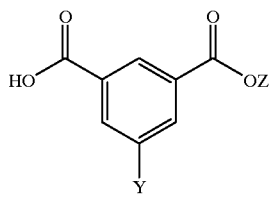

II (where Y is amino or nitro and Z is a carboxylic acid protecting group) to the solid support material, either directly or via a cleavable linker, L.

While a preferred embodiment employs 5-nitro-1,3-benzenedicarboxylic acid, 3-methylester as the central scaffold, it will be clear to anyone skilled in the art that the methods described herein can be extended to include the positional isomers, many of which are either commercially-available or known in the literature (i.e. 4-nitro-2-methylester-1,2-benzenedicarboxylic acid, 5-nitro-2-methylester-1,2-benzenedicarboxylic acid, 6-nitro-2-methylester-1,2-benzenedicarboxylic acid, 2-nitro-3-methylester-1,3-benzenedicarboxylic acid, 4-nitro-3-methylester-1,3-benzenedicarboxylic acid, 6-nitro-3-methylester-1,3-benzenedicarboxylic acid, 2-nitro-4-methylester-1,4-benzenedicarboxylic acid, 3-nitro-4-methylester-1,4-benzenedicarboxylic acid).

The invention also relates to a solid phase synthesis method that is suited to preparing a library of diverse compounds wherein all of said diverse compounds have a common benzenedicarboxylic acid scaffold, said method comprising the steps of:

(a) providing a solid phase support material;
(b) coupling a plurality of scaffold molecules either directly to the solid phase support material or indirectly to the solid phase support material via a cleavable linker, wherein said scaffold molecules have the general formula:

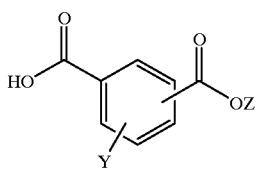

III where Y is nitro or amino, and Z is a carboxylic acid protecting group, and wherein free carboxylic acid groups of the scaffold molecules react with free amino or hydroxy group on said solid support material or said cleavable linker to form covalent amide or ester attachments;

(c) when Y is nitro, reduce said nitro to an amino group;
(d) optionally converting the amino group at position Y to a functional group selected from isocyanato and isothiocyanato;
(e) reacting one or more organic compounds having a suitable functional group with the amino, isocyanato or isothiocyanato group at position Y on the scaffold molecules whereby said functional group of said one or more organic compounds chemically reacts with the amino, isocyanato or isothiocyanato groups at position Y on said scaffold molecules;
(f) removing carboxylic acid protecting group Z from said scaffold molecule by hydrolysis to form free carboxylate groups on said scaffold molecules; and (g) reacting one or more organic compounds having a functional group capable of reacting with a free carboxylate group with the scaffold molecules such that the functional groups of said one or more compounds chemically react with the free carboxylate groups on said scaffold molecules.

Carboxylic acid protecting groups are well known in the art. The carboxylate is typically, but not exclusively protected by forming an ester. Various optionally substituted alkyl, trialkylsilyl, cycloalkyl, aralkyl and aryl groups are suitable for forming ester protecting groups. Green & Wuts, *Protective Groups in Organic Synthesis,* 2nd edition, Chapter 5 (John Wiley & Sons, New York) 1991.

By employing such scaffold-modified solid support materials and solid phase synthesis techniques described herein, it is possible to synthesize solid support materials having a plurality of pendant compounds covalently attached thereto, wherein said compounds have the formula

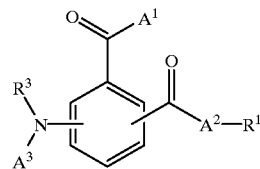

IV wherein
$A^1$ represents the point of attachment of a pendant compound to the solid support material, wherein said point of attachment is either directly to a pendant hydroxy or amino group on the solid support material or to an amino or hydroxy group on a cleavable linker that is attached to said solid support material;

$A^2$ is —O— or —$NR^2$—;

$A^3$ is $R^4CO$—, $R^4SO_2$—, $R^4R^5NC(O)$—, $R^4R^5NC(S)$— or $R^6OC(O)$—;

$R^1$, $R^4$, $R^5$ and $R^6$ are independently one of hydrogen or hydrocarbon, or when $A^3$ is $R^4R^5NC(O)$— or $R^4R^5NC(S)$—, then $R^4$ can be taken together with $R^5$ and the nitrogen to which $R^4$ and $R^5$ are attached to form a 4 to 7 member heterocyclic moiety, that is optionally substituted and optionally fused to one or two additional rings;

$R^2$ is one of hydrogen or hydrocarbon, or $R^2$ can be taken together with $R^1$ and the nitrogen to which $R^1$ and $R^2$ are attached to form a 4 to 6 member heterocyclic moiety, that is optionally substituted and optionally fused to one or two additional rings; and $R^3$ is hydrogen, alkyl, aralkyl, aryl, hydroxyalkyl, aminoalkyl, monoalkylamino($C_{2-10}$)alkyl, dialkylamino($C_{2-10}$)alkyl or carboxyalkyl.

These compounds attached to solid supports can be employed in lead compound discovery by testing such solid phase bound compounds in any suitable assay that is employed to screen for an industrially and/or medically useful activity. The compounds can also be clipped or cleaved from the solid phase to which they are attached to provide free compounds or mixtures of such compounds for testing. Advantages and disadvantages of these screening paradigms have been described elsewhere.

The libraries of the present invention comprise a plurality of structurally distinct compounds, present either as free compounds, or attached to a solid support material, said compounds all being of the general formula:

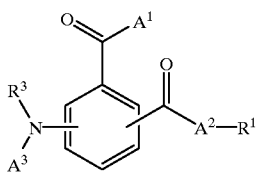

including salts thereof, wherein

A¹ is —OH, —NH₂, O—L —NH— or O—L —O—, where L is a direct bond or a cleavable linker and O— is a solid support material;

A² is —O— or —NR²—;

A³ is R⁴CO—, R⁴SO₂—, R⁴R⁵NC(O)—, R⁴R⁵NC(S)— or R⁶OC(O)—;

R¹, R⁴, R⁵ and R⁶ are independently one of hydrogen or hydrocarbon, or when A³ is R⁴R⁵NC(O)— or R⁴R⁵NC(S)—, then R⁴ can be taken together with R⁵ and the nitrogen to which R⁴ and R⁵ are attached to form a 4 to 7 member heterocyclic moiety, that is optionally substituted and optionally fused to one or two additional rings;

R² is one of hydrogen or hydrocarbon, or R² can be taken together with R¹ and the nitrogen to which R¹ and R² are attached to form a 4 to 6 member heterocyclic moiety, that is optionally substituted and optionally fused to one or two additional rings; and R³ is hydrogen, alkyl, aralkyl, aryl, hydroxyalkyl, aminoalkyl, monoalkylamino($C_{2-10}$)alkyl, dialkylamino($C_{2-10}$)alkyl or carboxyalkyl.

In one embodiment, the compounds exist in free form, that is, A¹ is —OH or —NH₂ In an alternate embodiment, the compounds are attached to a solid support material.

In a preferred embodiment, the libraries of the present invention comprise a plurality of compounds having formula V:

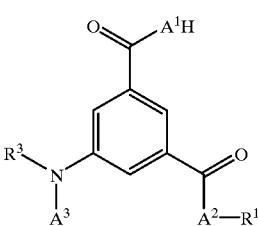

where A¹, A², A³, R¹–R⁶ are defined as above.

The term "hydrocarbon" as used herein includes straight-chained, branched and cyclic groups, including heterocyclic groups, containing up to 18 carbon atoms, suitably up to 15 carbon atoms, and conveniently up to 12 carbon atoms. Suitable hydrocarbon groups include $C_{1-8}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, $C_{3-7}$ cycloalkyl($C_{2-6}$)alkenyl, aryl, aryl ($C_{2-6}$) alkenyl, aryl($C_{2-6}$alkynyl, $C_{3-7}$heterocycloalkyl, $C_{3-7}$heterocycloalkyl($C_{1-8}$)alkyl, heteroaryl, heteroaryl ($C_{1-6}$)alkyl, heteroaryl($C_{2-6}$)alkenyl.

The hydrocarbon group, may in turn, be optionally substituted by one or more groups selected from hydroxy, nitro, trifluoromethyl, halogen, halo($C_{1-6}$)alkyl, $C_{1-6}$alkoxy, $C_{1-6}$alkoxy($C_{1-6}$)alkoxy, adamantyl, phenyl, benzyl, aryloxy, heteroaryl, heterocycloalkyl, keto, $C_{1-3}$ alkylenedioxy, cyano, carboxy, $C_{2-6}$ alkoxycarbonyl, $C_{2-6}$ alkoxycarbonyl($C_{1-6}$)alkyl, $C_{2-6}$ alkylcarbonyl, optionally substituted arylcarbonyl, $C_{1-6}$ alkylthio, $C_{1-6}$ alkylsulfinyl, $C_{1-6}$ alkylsulfonyl, arylthio, amino, mono- or di($C_{1-6}$) alkylamino, $C_{2-6}$ alkylcarbonylamino, $C_{2-6}$ alkoxycarbonylamino, $C_{2-6}$ alkoxycarbonylamino($C_{1-6}$) alkyl, amino($C_{1-6}$) alkoxy, amino($C_{1-6}$)alkyl, hydroxy($C_{1-6}$) alkyl, hydroxy($C_{1-6}$)alkoxy, $C_{2-6}$ carboxyalkyl, $C_{2-6}$ carboxyalkoxy, mono(($C_{1-6}$)hydroxyalkyl)amino, di(($C_{1-6}$) hydroxyalkyl)amino, mono(carboxy($C_{1-6}$)alkyl)amino, di(carboxy($C_{1-6}$alkyl)amino, $C_{1-6}$ alkoxycarbonylamino, $C_{1-6}$ alkoxycarbonyl, aryl($C_{2-6}$)alkoxycarbonyl, $C_{3-6}$ alkenylcarbonyl, $C_{3-6}$ alkynylcarbonyl, carboxy($C_{2-6}$) alkoxycarbonyl, $C_{2-6}$ alkanoyl, $C_{2-6}$ alkoxycarbonyl, phenyl ($C_{2-6}$)alkoxycarbonyl, carbamoyl, $C_{2-6}$ alkylcarbamoyl, hydroxy($C_{2-6}$)alkylcarbamoyl, di(($C_{2-6}$)alkyl)carbamoyl, amino($C_{2-6}$)alkylcarbamoyl, cycloalkylcarbamoyl, cycloalkyl($C_{2-6}$)alkylcarbamoyl, N-hydroxycarbamoyl, N-($C_{2-6}$)alkenyloxy carbamoyl, phosphono, $C_{1-6}$ alkylphosphono, di(($C_{1-6}$)alkyl)phosphono, tri(($C_{1-6}$)alkyl) alkylphosphono, $C_{1-6}$ alkylsulfonyl, $C_{2-6}$ alkenylsulfonyl, $C_{2-6}$ alkynylsulfonyl, $C_{1-6}$ alkylsulfinyl, arylthio, $C_{1-6}$ alkylthio, $C_{1-6}$ alkylsulfonamido, amidino, guanidino, $C_{1-6}$ alkyliminoamino, formyliminoamino, trifluoromethoxy or perfluoroethoxy, and when any of R¹, R⁴, R⁵ and R⁶ are other than alkyl, said group may also be substituted with one or two lower alkyl moieties.

The term "alkyl" is used herein to mean a straight or branched chain radical of 1 to 20 carbon atoms, unless the chain length is limited thereto, including, but not limited to methyl, ethyl, n-propyl, isopropyl, n-butyl, sec-butyl, isobutyl, tert-butyl, pentyl, hexyl, heptyl and the like. Preferably the alkyl chain is 1 to 10 carbon atoms in length, more preferably 1 to 8 carbon atoms in length, most preferably from 1 to 4 carbon atoms in length.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-l-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "cycloalkyl" as employed herein by itself or as part of another group refers to cycloalkyl groups containing 3 to 9 carbon atoms, preferably 4 to 7 carbon atoms. Typical examples are cyclopropyl, cyclobutyl, cyclopentyl, cyclohexyl, cycloheptyl, cyclooctyl and cyclononyl.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "aralkyl" or "arylalkyl" as employed herein by itself or as part of another group refers to $C_{1-6}$ alkyl groups having an aryl substituent, such as benzyl, phenylethyl, phenylpropyl or 2-naphthylmethyl.

The term "heterocyclic" is used herein to mean a saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Examples include, but are not limited to, pyrrolidine, piperidine, piperazine, morpholine, imidazolidine, pyrazolidine, benzodiazepines, and the like.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_6$ alkyl, or together with the nitrogen to which they are bound, form a saturated or unsaturated 5-, 6-, or 7-membered ring.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolinyl, isoquinolinyl, tetrahydroquinolinyl, phthalazinyl, naphthyridinyl, quinazolinyl, cinnolinyl, pteridinyl, 4αH-carbazolyl, carbazolyl, β-carbolinyl, phenanthridinyl, acridinyl, phenanthrolinyl, phenazinyl, isothiazolyl, phenothiazinyl, isoxazolyl, furazanyl and phenoxazinyl groups). Particular heteroaryl groups are pyridyl, furyl, benzofuryl, thienyl, benzthienyl, pyrrolyl, indolyl and oxadiazolyl.

Particular heteroaryl($C_{1-6}$)alkyl groups include indolylethyl, indolylpropyl, pyridylmethyl and furylmethyl.

Particular heterocycloalkyl groups include piperidyl, piperazinyl, and morpholinyl.

The term "halogen" or "halo" as employed herein by itself or as part of another group refers to chlorine, bromine, fluorine or iodine with chlorine being preferred.

The terms "core structure" or "scaffold" are used herein to mean a molecular structure that includes reactive sites for attaching organic moieties, including functional groups, to the scaffold such that a desired spacial orientation of the organic moieties is obtained. Preferably, the core structure or scaffold is derived from compounds which have been shown to interact with a biological receptor, and is thereafter used as a template for designing the libraries of compounds to be made. The preferred core structures that are employed in the present invention have formula IV–V, as defined herein.

The term "library of compounds" is used herein to mean an array or plurality of compounds derivatized from a common core structure. Suitably, the core structure used for designing a library of compounds are formula IV–V.

The term "virtual library" is used herein to mean any collection of chemical entities that can be reliably synthesized "on demand" using one or more previously optimized synthetic schemes such as those described in this application. The chemical structures, relevant molecular descriptors or representations, the method and reagents required for synthesis of those chemical entities are stored in an appropriate electronic medium (such as a database). From this collection of chemical entities, computer algorithms select a group of virtual library members for synthesis (sub-library) which collectively best satisfy a set of selection criteria as determined by the user or some automated procedure.

The term "combinatorial library" is used herein to mean a collection of compounds based upon a core structure, wherein the library contains a discrete number of independently variable substituents, functional groups or structural elements, and further, wherein the library is designed so that, for the range of chemical moieties selected for each of the independently variable substituents, compounds containing all possible permutations of those substituents may be present in the library. The methods for preparing combinatorial sub-libraries of compounds of the present invention are such that molecularly diverse compound members of the libraries are synthesized simultaneously.

The term "solid phase synthesis" means one or a series of chemical reactions used to prepare either a single compound or a library of molecularly diverse compounds, wherein the chemical reactions are performed on a compound that is bound to a solid phase support material through an appropriate linkage.

The term "resin-bound synthesis" means one or a series of chemical reactions used to prepare either a single compound or a library of molecularly diverse compounds, wherein said chemical reactions are performed on a compound that is bound to a polymeric resin support through an appropriate linkage.

The terms "resin," "inert resin," polymeric resin" or "polymeric resin support" are used herein at all occurrences to mean a bead or other solid support such as beads, pellets, disks, capillaries, hollow fibers, needles, solid fibers, cellulose beads, pore-glass beads, silica gels, grafted co-poly beads, poly-acrylamide beads, latex beads, dimethylacrylamide beads optionally cross-inked with N,N'-bis-acryloyl ethylene diamine, glass particles coated with a hydrophobic polymer, etc., i.e., a material having a rigid or semi-rigid surface, and preferably a mesh size of greater than 50.

The term "G-protein coupled receptor" is used herein to mean a membrane receptor using G-proteins as part of their signaling mechanism, including, but not limited to muscarinic acetylcholine receptors, adenosine receptors, adrenergic receptors, IL-8R receptors, dopamine receptors, endothelin receptors, histamine receptors, calcitonin receptors and angiotensin receptors.

The term "assay" is used herein to mean a binding assay or a functional assay known or obvious to one of ordinary skill in the art, including, but not limited to, the assays disclosed herein.

Preferably, the libraries of the present invention comprise a plurality of compounds having formula IV or V, wherein:

$R^1$, $R^4$, $R^5$ and $R^6$ are independently one of hydrogen, $C_{1-12}$ alkyl, $C_{4-7}$ cycloalkyl, $C_{4-7}$ cycloalkyl($C_{1-12}$) alkyl, $C_{2-8}$ alkenyl, $C_{5-7}$ cycloalkenyl, $C_{5-7}$ cycloalkenyl($C_{1-8}$)alkyl, $C_{2-8}$ alkynyl, $C_{6-14}$ aryl, $C_{6-14}$ aryl($C_{1-8}$)alkyl, $C_{3-8}$ heterocycloalkyl($C_{1-8}$)alkyl, heteroaryl or heteroaryl($C_{1-8}$)alkyl, any of which is optionally substituted, and where any of said cycloalkyl, cycloalkenyl, aryl, heterocycloalkyl or heteroaryl rings are optionally fised to one or two additional rings, or when $A^3$ is $R^4R^5NC(O)$— or $R^4R^5NC(S)$—, then $R^4$ can be taken together with $R^5$ and the nitrogen to which $R^4$ and $R^5$ are attached to form a 4 to 7 member heterocyclic moiety, that is optionally substituted and optionally fused to one or two additional rings;

$R^2$ is one of hydrogen, $C_{1-12}$ alkyl, $C_{4-7}$ cycloalkyl, $C_{4-7}$ cycloalkyl($C_{1-12}$)alkyl, $C_{2-8}$ alkenyl, $C_{5-7}$ cycloalkenyl, $C_{5-7}$ cycloalkenyl($C_{1-8}$)alkyl, $C_{2-8}$ alkynyl, $C_{6-14}$ aryl, $C_{6-14}$ aryl($C_{1-8}$)alkyl, $C_{3-8}$ heterocycloalkyl($C_{1-8}$)alkyl, heteroaryl or heteroaryl($C_{1-8}$)alkyl, any of which, except for hydrogen, can be optionally substituted, or $R^2$ can be taken together with $R^1$ and the nitrogen to which $R^1$ and $R^2$ are attached to form a 4 to 7 membered heterocyclic ring that can include up to two additional heteroatoms selected from oxygen, sulfur and nitrogen, and can be optionally substituted and optionally fused to one or two additional rings; and $R^3$ is hydrogen, $C_{1-12}$ alkyl, $C_{6-14}$ aryl($C_{1-8}$)alkyl, $C_{6-14}$ aryl, $C_{1-12}$ hydroxyalkyl, $C_{1-12}$ aminoalkyl, monoalkylamino($C_{2-10}$)alkyl, dialkylamino($C_{2-10}$) alkyl or $C_{1-12}$ carboxyalkyl.

Preferred values of $R^1$, $R^4$, $R^5$ and $R^6$ include $C_{1-8}$ alkyl, $C_{4-7}$ cycloalkyl, $C_{2-8}$ alkenyl, $C_{6-10}$ aryl, or $C_{6-10}$ aryl ($C_{1-8}$)alkyl, optionally substituted by one to three substituents independently selected from the groups listed in the following paragraph. Additional preferred values include $C_{3-8}$ heterocycloalkyl($C_{1-8}$)alkyl, heteroaryl or heteroaryl ($C_{1-8}$)alkyl, optionally substituted by one to three substituents independently selected from the groups listed in the following paragraph.

Preferred optional substituents include: hydroxy, nitro, trifluoromethyl, halogen, $C_{1-6}$ alkoxy, phenyl, aryloxy, cyano, carboxy, $C_{2-6}$ alkoxycarbonyl, amino, mono- or di($C_{1-6}$)alkylamino, $C_{1-6}$ alkylsulfonyl, $C_{1-6}$ alkylsulfonamido, amidino, and guanidino.

Suitable values of $R^4$, $R^5$ and $R^6$ include phenyl, methyl, ethyl, propyl, 2-butoxyethyl, cyclohexylethyl, cyclooctylmethyl, 3,3-dimethyl-1-butyl, 4-biphenylmethyl, 4-ethoxy-3-methoxyphenethyl, 3,3-diphenyl-1-propryl, 4-cycloheptenyl, 4-nitrophenyl, 2-phenylcyclopropyl, adamantylmethyl, pinanemethyl, 2-norbornanylmethyl, 2-indanylmethyl, fluorenyl, 9-xanthenyl, 4-morpholinylethyl, 2-tetrahydrofurfurylmethyl, 2-thiophene, and 4-methyl-5-thiazolylmethyl.

Suitable values of $R^1$ and $R^2$ include aminopentyl, aminobutyl, benzyl, phenyl, 2-pyridylethyl, 4-pyridylethyl, dansylaminopentyl, 4-morpholinylethyl and 4-piperidylmethyl. When $R^1$ and $R^2$ are taken together to form a heterocyclic ring, additional values include N-iminodibenzyl, N-phenothiazine and N-carbazole.

Preferred values of $R^2$ include $C_{1-8}$ alkyl, $C_{4-7}$cycloalkyl, $C_{2-8}$ alkenyl, $C_{6-10}$ aryl, $C_{6-10}$ aryl($C_{1-8}$)alkyl, heteroaryl or heteroaryl($C_{1-8}$)alkyl, optionally substituted by one to three substituents that are recited in the previous paragraph.

Preferred values of $R^3$ include hydrogen, $C_{1-8}$ alkyl, $C_{1-8}$ hydroxyalkyl, $C_{1-8}$ aminoalkyl, monoalkylamino($C_{2-8}$) alkyl, dialkylamino($C_{2-8}$)alkyl or $C_{1-8}$ carboxyalkyl.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

Certain compounds of the libraries may also be solvated, especially hydrated, where the compounds are hygroscopic. Hydration may occur during manufacturing of the compounds or compositions comprising the compounds, or the hydration may occur over time due to the hygroscopic nature of the compounds.

The present invention allows for the synthesis and assembly of sublibraries of compounds with diverse substitutions on a common aryl core structure. Compounds that are accessible by the present invention include compounds having the following covalent attachments to the aryl moiety of the scaffold: thiourea (formula 7', Scheme 5), urea (formula 11', Scheme 6), carbamate (formula 14', Scheme 7), sulfonamides (formula 18', Scheme 8 and formula 20', Scheme 9), amides (formula 26', Scheme 11 and formula 7', Scheme 11), as well as positional isomers of these compounds formed by employing a different aminobenzenedicarboxylic acid starting material. Tables 1–4 exemplify the various types of groups that can be attached at $R^1$ through $R^6$.

The compounds of the present invention or the plurality of compounds can exist singly or as a mixture in one or more containers; or singly or a mixture in a plurality of containers that are packaged together (for example a set of vials or microtiter plates).

The plurality of compounds may singly in a plurality of containers (one compound per container), as a mixture in a single container, or as mixtures in a plurality of containers. A container, for purposes of the present invention, is any substrate on or in which compounds or resin-bound compounds can be stored. Examples of commercially useful containers includes single vials, test tubes or ampules, or microtiter plates that typically have 96 or 384 wells per plate. Thus, a collection of compounds may comprise a plurality of containers, m, that are packaged together, and each container includes one or more compounds, n, to provide m×n compounds, wherein m is 1 to 100,000 and n is 1 to 500, more preferably, wherein m is 10 to 500 and n is 1 to 20.

The compounds (or libraries of compounds) of the present invention may either remain bound to the solid support material preferably a resin, which is used to perform the resin-bound synthesis (hereinafter referred to as resin-bound compounds (or solid-support bound compounds)) or not bound to a resin (hereinafter referred to as soluble or free compounds).

In an additional aspect of the invention, the invention includes a kit comprising a plurality of solid phase bound compounds or compounds in solution. Additionally, when the compounds are bound to the solid phase, the kit can be supplied with the reagents necessary for "clipping" the compounds from the solid phase. Separate vials or wells can be employed to separate compounds or solid-phase bound compounds. In one embodiment, vials or wells themselves can be the solid support, or polymeric pins that can be lowered into an appropriate contained can serve as the solid support. For example, vials or wells constructed from the appropriate material can themselves serve as the solid support material. In a preferred embodiment, polymeric beads serve as the solid support.

An important aspect of the present invention is the synthesis of a combinatorial library that has a large degree of chemical diversity. Chemical diversity of the collection is increased, at one level, by varying both the type of linkage employed and the nature of the groups that become coupled to the free amino moiety of the scaffold. For example, reaction of resin bound amine with a suitably activated carboxylic acid forms an amide linkage. Reaction of the amino functionality with a sulfonyl chloride provides a sulfonamide linkage. Or, the amino functionality is first modified to provide a distinct functional group. For instance, the amino group can be converted to an isocyanate group. Thereafter, the isocyanate group is reacted with various alcohols to form carbamate analogs of the scaffold. Diversity of the library is also enhanced by employing reagents that bear functional groups which introduce a range of chemical properties and/or defined steric configurations. Thus, the various functional groups are attached to different linker portions (formed by reaction of two complementary functional groups, one on the scaffold and one on a reactant).

Figure 2:
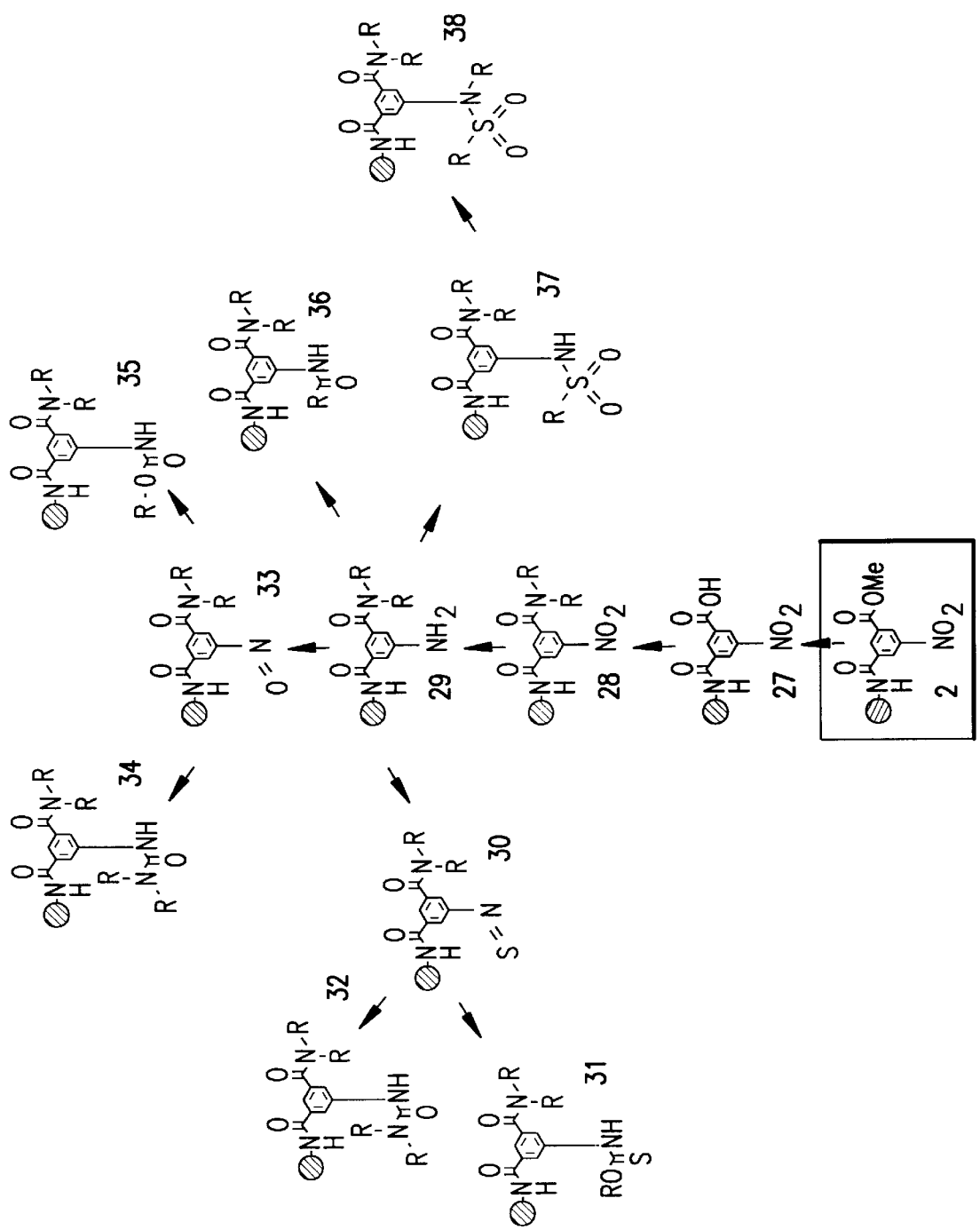
FIG. 2 depicts a synthesis tree that employs an alternative scheme to synthesize a diverse series of compounds sharing a common scaffold structure. In this tree, the ester groups of resin 2 are hydrolyzed and coupled with amines before the nitro groups are reduced and the resulting anilines elaborated by reaction with various organic compounds having a functional group capable of reacting with the free amino groups on the resin.

The library trees shown in FIG. 1 and FIG. 2 are based on a common scaffold, resin-bound 3-methyl ester-5-nitrobenzenedicarboxylic acid (resin 2). This scaffold is a preferred scaffold of the present invention. In FIG. 1, the nitro group of resin 2 is reduced and the resulting aniline is further reacted, in either one or more additional steps, to give thiourea 5, urea 9, carbamate 12, sulfonamide 15, alkylated sulfonamide 16, amide 21, or alkylated amide 24. The methyl ester group of each compound is then hydrolyzed to the corresponding carboxylic acid 6, 10, 13, 17, 19, 22, or 25 and coupled with various amines to give amides 7, 11, 14, 18, 20, 23 or 26. By coupling amines with carboxylic acids in the final step, dinucleophilic amines (diamines and amino alcohols) can be employed to functionalized this position in each product. Dinucleophilic amines cannot be employed in earlier steps (such as to form urea 9 from isocyanate 8) because of intermolecular reaction of the second nucleophilic site with a neighboring activated carboxylic acid during the final diversification step (10–11).

More detailed descriptions of the synthesis of resins representing the trunk (resin 3) and branches (resins 7, 11, 14, 18, 20, 23, and 26) of the synthetic scheme shown in FIG. 1 are shown in Schemes 4–11 hereinbelow.

In FIG. 2, the methyl ester of resin 2 is hydrolyzed and coupled with amines before the nitro group is reduced and the resulting aniline elaborated, which is the reverse strategy to FIG. 1. Thus, dinucleophilic amines can be employed to make urea 34 from isocyanate 33. However, in this scheme, dinucleophilic reagents (such as amino alcohols) cannot be used to make amide 28 from carboxylic acid 27 due to incompatibility issues in later steps.

Figure 3:
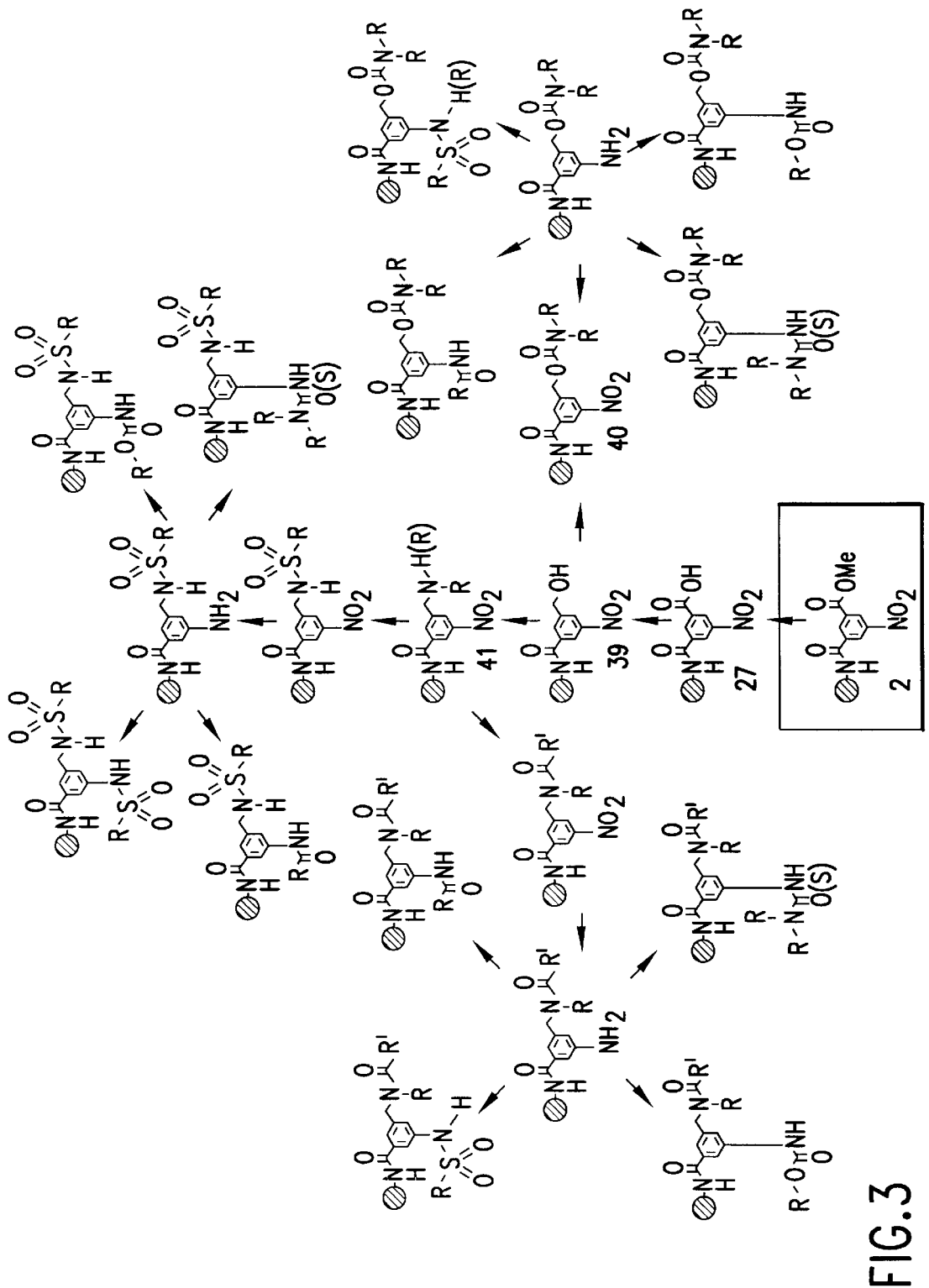
FIG. 3 depicts a synthesis tree that employs an alternative scheme to synthesize a diverse series of compounds that share a common scaffold that differs from the scaffold of Schemes 1 and 2. In Scheme 3, the ester group of resin 2 is hydrolyzed and the resulting resin-bound carboxylic acid (resin 27) is reduced to the corresponding alcohol 39. The alcohol functionality is then modified. Finally, the nitro groups are reduced and the free amino groups are elaborated.
Figure 4:
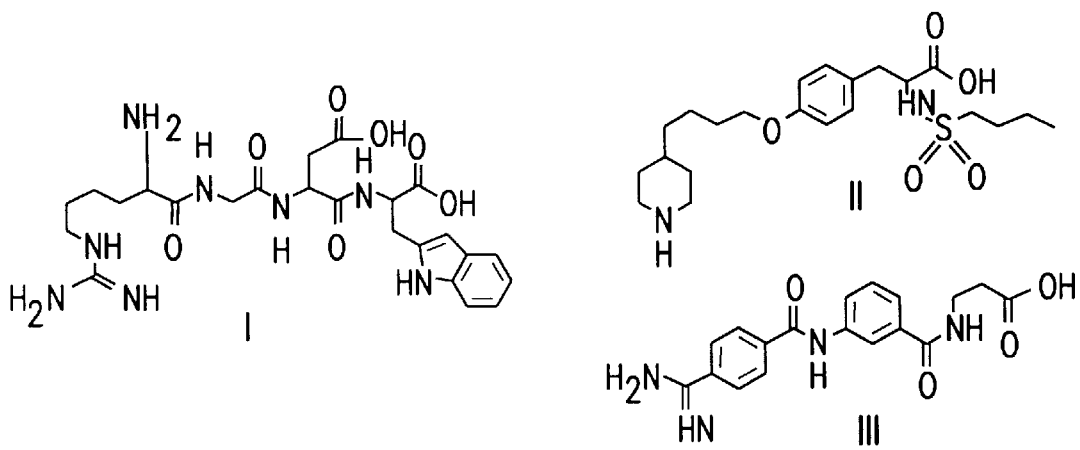
FIG. 4 depicts a number of prior art compounds that are discussed in the Background of the Invention section.
Figure 4:
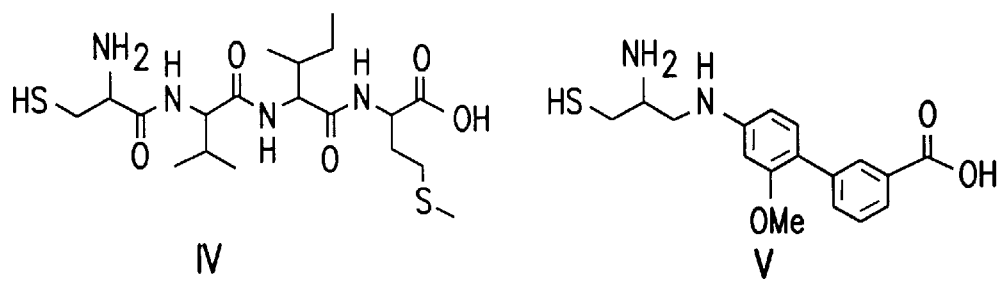
Figure 4:
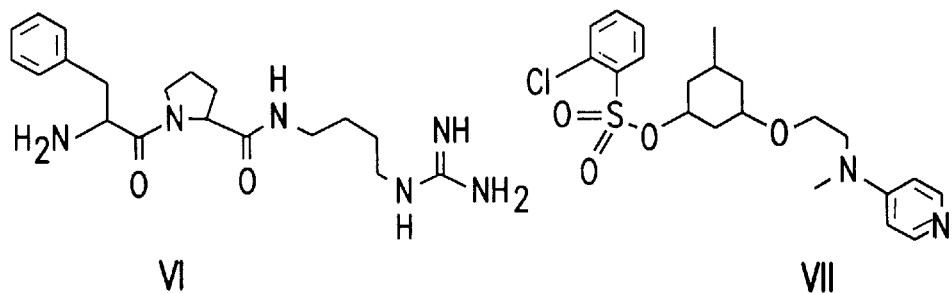

FIG. 3 illustrates that solid-support bound scaffolds of the current invention are also readily modified by known synthetic techniques. For instance, transformation of the methyl ester of resin 3 (FIG. 3) using common synthetic sequences known in the art provides the corresponding resin-bound alcohol 39 (alternatively, resin-bound alcohol 39 may be prepared directly by coupling the known 3-hydroxymethyl-5-nitro-benzenecarboxylic acid to an amino group or hydroxy group on a solid support or to an amino or hydroxy group on a cleavable linker that is attached to said support material). Resin-bound alcohol 39 serves as a key common intermediate to a variety of related analogs: two examples are illustrated in FIG. 3. Resin-bound alcohol 39 can be transformed into resin-bound carbamate 40 by treatment with triphosgene followed by addition of alkyl or aryl amines. Similarly, resin-bound alcohol 39 can be transformed into resin- bound benzylamine analogs 41 via treatment of the corresponding resin-bound benzylhalide with alkyl and aryl amines. Additional diversity elements can be introduced to resin-bound carbamates 40 and benzylamine analogs 41 using methods described herein. Other chemical transformations of resin-bound alcohol 39 will be obvious to those skilled in the art.

In one illustrative embodiment, functional groups appended to the core structure are selected for their potential to interact with, and preferably modulate enzymes or receptors. One example includes constructing compounds that can inhibit proteases. Thus, compounds of the present invention can be used for the various utilities associated with protease inhibition, which are detailed further herein. Compounds can be constructed that possess aromatic and/or polar groups that facilitate binding of the compounds to the active site of a protease. It is to be emphasized however, that the great diversity achievable by the use of the scaffold and synthesis steps described herein make the present libraries useful as a source of lead compounds against any number of biological targets. Such diversity allows the library of the present invention to be employed in any known high-throughput assay to determine a particular activity of individual compounds and closely related analogs.

Preferably, libraries and sub-libraries of the present invention are prepared as discrete compounds using parallel, robotic, high-throughput synthetic techniques. To prepare large quantities of a particular resin for later reaction in separate wells or vessels, a batch mode may be employed, such that a large quantity of one resin can be synthesized, and thereafter divided into separate wells or vessels. Alternatively, the same reaction is carried out in a parallel manner in multiple reaction vessels. The attachment of the scaffold moiety to the solid support is preferably conducted in batch mode, with the resulting scaffold-solid support conjugates being distributed into multiple reaction vessels for further reaction.

Upon identification of compounds in a first phase of screening, further modifications can be made to the contents of the libraries. For example, if a first iteration of screening results in an active compound that contains a phenyl ring, then in subsequent iterations of the screen this aromatic residue can be varied using substituted phenyl groups in a stepwise manner. A preferred iterative method is DirectedDiversity®, which is described in U.S. Pat. No. 5,463,564, fully incorporated by reference herein.

DirectedDiversity® is an iterative drug refinement process that explores chemical space through successive rounds of sublibrary selection from a virtual library followed by synthesis and biological evaluation of that sublibrary. The results of this computer-aided, iterative process are chemical entities with a prescribed set of physical and biological properties. For pharmaceutical applications, the prescribed set of properties are those desired for preclinical drug candidates such as potency and selectivity.

Central to this iterative process is a large collection of chemical structures that can be reliably synthesized "on demand" using one or more previously optimized synthetic schemes such as those described in this application. This collection of readily prepared compounds is referred to as a "virtual library." It is from this virtual library that computer algorithms select those virtual library members for synthesis that are predicted to best reflect the desired biological and chemical properties. If, after biological screening, none of the molecules in the initial sublibrary meet the desired set of criteria, the resulting SAR information is fed back into the selection process, a new sublibrary is selected and the cycle is repeated.

Using the DirectedDiversity® technique, a diverse sublibrary is initially selected from the virtual library, synthesized, and assayed for biological activity. If no active molecules are identified, a second sublibrary is rapidly selected that complements the initial sublibrary. If however, an active molecule(s) is identified in a sublibrary and, for example, contains a phenyl ring, then subsequent sublibraries are likely to contain related molecules that help to refine and differentiate SAR models. Such a technique couples rational selection of screening candidates (sublibraries) with efficient high-throughput methods of synthesis and biological screening. Thus, the present invention provides a solution to inefficient lead discovery in fields where organic molecules having the core structure or scaffolds of the present invention possess activity.

Reactants and scaffolds bearing protected or unprotected functional groups are prepared using the procedures described herein. If a functional group is such that it will react with other moieties or reagents during subsequent steps, the functional group is protected with a protecting group. The protecting group is then removed at an appropriate step of the synthesis. The scaffold(s) employed in the present invention inherently possess a protected carboxylic acid moiety (ester), thereby allowing the synthesis to proceed in an unambiguous stepwise manner. Other protecting groups are well known in the synthesis of both non-peptide and peptide molecules. For example, a rich variety of esters and amides can be employed as hydroxyl protecting groups for the carboxylic acid moiety. Amino groups can also be protected by a variety of amino protecting groups, including t-butoxycarbonyl (BOC) and benzyloxycarbonyl (CBZ). See Greene, T. W. and Wuts, P. G. M., *Protective Groups in Organic Synthesis,* 2nd Edition, John Wiley and Sons, Inc., New York (1991).

Abbreviations

BOP: benzotriazolyl-N-oxy-tris(dimethylamino) phosphonium hexafluorophosphate (Castro's Reagent)

PyBOP: benzotriazol-1-yl-oxytripyrrolidinophosphonium hexafluorophosphate

HBTU: O-benzotriazol-1-yl-N,N,N',N'-tetramethyluronium hexafluorophosphate

TBTU: O-benzotriazol-1-yl-N,N,N',N'-tetramethyluronium tetrafluoroborate

CDI: 1,1'-carbonyldiimidazole (carbodiimidazole)

DCC: N,N'-dicyclohexyl carbodiimide

DIC: N,N'-diisopropyl carbodiimide

FMOC: 9-fluorenylmethoxycarbonyl protecting group

MBHA: methylbenzhydrylamine

HOAt: 1-hydroxy-7-azabenzotriazole

TFA: trifluoroacetic acid

DMF: dimethylformamide

DEAD: diethyl azodicarboxylate

DBU: 1,8-diazabicyclo[5.4.0]undec-7-ene

HATU: N-[(dimethylamino)- 1H-1,2,3 -triazolo[4,5-b]pyridin-1-yl methylene]-N-methylmethanaminium hexafluorophosphate N-oxide Methods of Making Resins and Compounds of the Invention A large amount of practical experience exists in the synthesis of peptides on solid supports. For example, Lam et al., *Nature* 354:82 (1991) and (WO 92/00091) disclose a method of synthesis of linear peptides on a solid support such as polystyrene or polyacrylamide resin; Geysen et al., *J. Immunol. Meth.,* 102:259 (1987) discloses the synthesis of peptides on derivatized polystyrene pins which are arranged on a block in such a way that they correspond to the arrangement of wells in a 96-well microtiter plate (pin-based synthesis).

A wide variety of organic reactions can be carried out on substrates immobilized on resins. These include, in addition to peptide synthesis reactions which are well known to those of ordinary skill in the art, nucleophilic displacements on benzylic halides, halogenation, nitration, sulfonation, oxidation, hydrolysis, acid chloride formation, Friedel-Crafts reactions, reduction with $LiAlH_4$, metallation, and reaction of the organometallic polymer with a wide variety of reagents. See, for example, N. K. Malhur et al., *Polymers as Aids in Organic Chemistry,* Academic Press, New York, p. 18 (1980); Farrall et al., *J. Org. Chem.* 41:3877 (1976); Gordon et al., *J. Med Chem.* 37:1387–1401 (1994); Terrett et al., *Tetrahedron* 51:8135–8173 (1995); Hermkens et al., *Tetrahedron* 52:4526–4554 (1996); Lebl, M. "Dynamic database of papers published in the field of molecular diversity," INTERNET, http://vesta.pd.com/oth_info. (constantly updated).

Multistep synthesis on a solid phase has a number of advantages over traditional solution phase synthesis. Primary among them is the ease of post-reaction processing which often simply involves simple filtration and washing of the resin. For this reason, large excesses of reagents and reactants can often be employed to drive reactions to completion. Further benefits of synthesis on solid phase include simulation of high dilution conditions, stabilization of reactive intermediates, and ease of handling. Owing to the simplicity of post-synthesis processing, automation is rapidly emerging that allows chemists to rapidly prepare discrete compounds in parallel or as mixtures via a mix and split strategy (see Furka et al., *Int. J. Peptide Protein Res.* 37:487–493 (1991). Thus, compounds of the present invention can be synthesized either as discrete entities or as mixtures.

The advantages of solid phase synthesis are balanced by a number of additional complexities and challenges. Chief among them is the attachment of a reaction component or scaffold to a solid support and subsequently a strategy for cleavage of the final compounds of interest from that support. Additional challenges include monitoring reactions on a solid phase, requirement for clean high yielding reactions, compatibility of solid phase/linker to reaction conditions, and influence of the polymeric support on selectivity and reaction rate.

Preferably, the solid phase support is a polymeric material that is inert to the conditions of synthesis. Many polymeric solid phase supports are known in the art. Historically, these supports found utility in peptide synthesis. The earliest supports were partially crosslinked polystyrene beads. While Merrifield first described a chloromethyl derivatized polystyrene support (see Merrifield, R. B., *J. Am. Chem. Soc.* 85: 2149–2154 (1963)), many derivatized or composite polystyrene supports are now commercially-available and well known to those familiar to the art. Examples include aminomethyl polystyrene (1% divinylbenzene cross-linked); 2-chlorotrityl chloride polystyrene (Calbiochem-Novabiochem Corp.); 4-methyl benzyhydrylamine resin (MBHA, Calbiochem-Novabiochem Corp.); Sieber amide resin (Calbiochem-Novabiochem Corp.). More recently, solid supports based on more hydrophilic polymers have been introduced. These supports tend to offer improved swelling characteristics with a wider variety of solvents (especially protic solvents) compared to solely polystyrene-based supports. Examples include polyethylene glycol-polystyrene graft co-polymer resins (i.e. Tentagel, TG, Rapp Polymere Gmbh), ArgoGel (Argonaut Technologies), bis-2-acrylamidoprop-1-yl polyethyleneglycol crosslinked dimethylacrylamide (PEGA, Calbiochem-Novabiochem Corp.) and polyamide resins (i.e. NovaSyn K 125, NovaSyn P500, Calbiochem-Novabiochem Corp.).

Resins and supports for solid phase synthesis can also have a variety of physical shapes. Although the most common is a spherical bead, polyacrylic-grafted polyethylene extrusions called 'pins' (see Virgilio et al., *Int. J. Peptide Protein Res.* 42:1–9 (1993)) are another common shape.

Other materials which are employed in solid phase synthesis include cellulose in the form of 'Perloza' beads (see Englebretsen et al, *Int. J. Peptide Protein Res.* 40:487–496 (1992)), paper (see Frank et al., *Tetrahedron* 44:6031–6040 (1988)) and cotton (see Lebl et al., *Innovation and Perspectives in Solid Phase Synthesis; 2nd Intl. Symposium,* Epton, R., ed., Intercept Ltd., Andover (1992), pp. 251–257).

Polymeric supports that are soluble in many organic solvents yet are easily precipitated to aid purification and handling are also readily available (see Janda et al., *Proc. Natl. Acad. Sci. USA* 92:6419 (1995)).

While some of these supports described above are derivatized such that scaffolds can be readily attached and the products subsequently cleaved, many of these solid supports require the use of an appropriate linker. The linker group may be any group that can react with the solid support and a scaffold. The linker group can be pre-attached to the solid support or a linker can first be reacted with the scaffold moiety and thereafter attached to the solid support. The linker must be stable to the reaction conditions that are employed during any synthesis step wherein the linker serves to attach the scaffold to the solid support, but should be capable of releasing the desired compound upon completion of the synthesis. The release or cleavage is preferably mediated by some specific, regulatable mechanism. Such regulatable methods include but are not limited to thermal, photochemical, electrochemical, acid, base, oxidation, and reduction reactions.

Many linkers are known in the art and an ever-increasing number are commercially available. For example, acid labile linkers bearing a hydroxyl group, such as 4-hydroxymethylphenoxy aliphatic acids, permit coupling of the scaffold or reagent to the linker via ether, acetal or ester linkages. Acid labile linkers bearing an amine, such as p-[2,4-dialkoxyaminobenzyl]phenoxy acetic acid, link molecules through functional groups such as amides, imines, carbonates, or ureas. The number and location of the alkoxy substituents on the aromatic rings of these linkers determine the ease of cleavage of the desired molecules from the solid support under acidic conditions. Trityl-based linkers can also be cleaved under mild acidic conditions. A variety of base-labile linkers are available and include [4-(2-bromoproprionyl)phenoxy]acetic acid. When this linker is employed, acid, ester and amide derivatives of the organic compound can be obtained via cleavage of the resultant ester bond with nucleophiles such as hydroxide, alkoxides, and amines. In addition, the [4-(2-bromopropionyl) phenoxylacetic acid linker as well as a variety of ortho-nitrobenzyl linkers enable the photochemical cleavage of an organic compound from solid support under neutral conditions.

The preferred polymer resins for use herein employ a Rink amide linker (see Rink, H., *Tetrahedron Lett.* 28:3738 (1987)) or a xanthydrylamine linker (see Sieber, P., *Tetrahedron Lett.* 28:2107 (1987)) which provides carboxamides (—CONH$_2$) following treatment of the resin with acid (TFA). These linkers can be attached to a variety of polymer types which include functionalized crosslinked polystyrene, polyethylene glycolpolystyrene graft co-polymer resins (i.e. Tentagel, TG (Rapp Polymere Gmbh), ArgoGel (Argonaut Technologies), and bis-2-acrylamidoprop-1-yl polyethyleneglycol crosslinked dimethylacrylamide (PEGA, Calbiochem-Novabiochem Corp.) and other solid phase supports known and obvious to one of ordinary skill in the art. The preferred solid support for use herein are the Rink Amide MBHA (Calbiochem-Novabiochem Corp.). Less preferred are NovaSyn® TGR (Calbiochem-Novabiochem Corp.), Rink Amide PEGA (Calbiochem-Novabiochem Corp.), NovaSyn® TG Sieber resin (Calbiochem-Novabiochem Corp.), and Sieber Amide Resin (Calbiochem-Novabiochem Corp.).

The following schemes illustrate the preparations of functionalized resins 2 and 3, and the synthesis of a library according to FIG. 1.

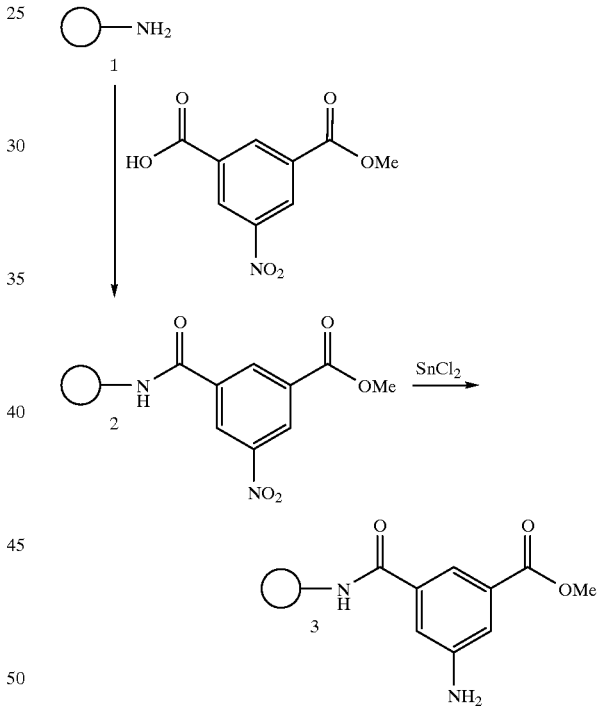

Scheme 4
Synthisis of Resin 3

Scheme 4 illustrates the formation of resin 3. Resin 3 is a key synthetic intermediate for all products in the Scheme 1 library tree. FMOC-deprotected Rink amide MBHA resin 1 was coupled with commercially available 5-nitro-1,3-benzenedicarboxylic acid, 3-methyl ester to give resin 2. The aromatic nitro group on resin 2 was reduced with tin (II) chloride to give aniline resin 3. ○—NH$_2$ represents a solid phase support having a plurality of pendant amino groups. In the examples herein, the pendant amino groups are present on the cleavable Rink linker which is covalently attached to polystyrene (1% DVB crosslinked, 100–200 mesh) functionalized with a 4-methylphenyl-aminomethyl group (MBHA polystyrene).

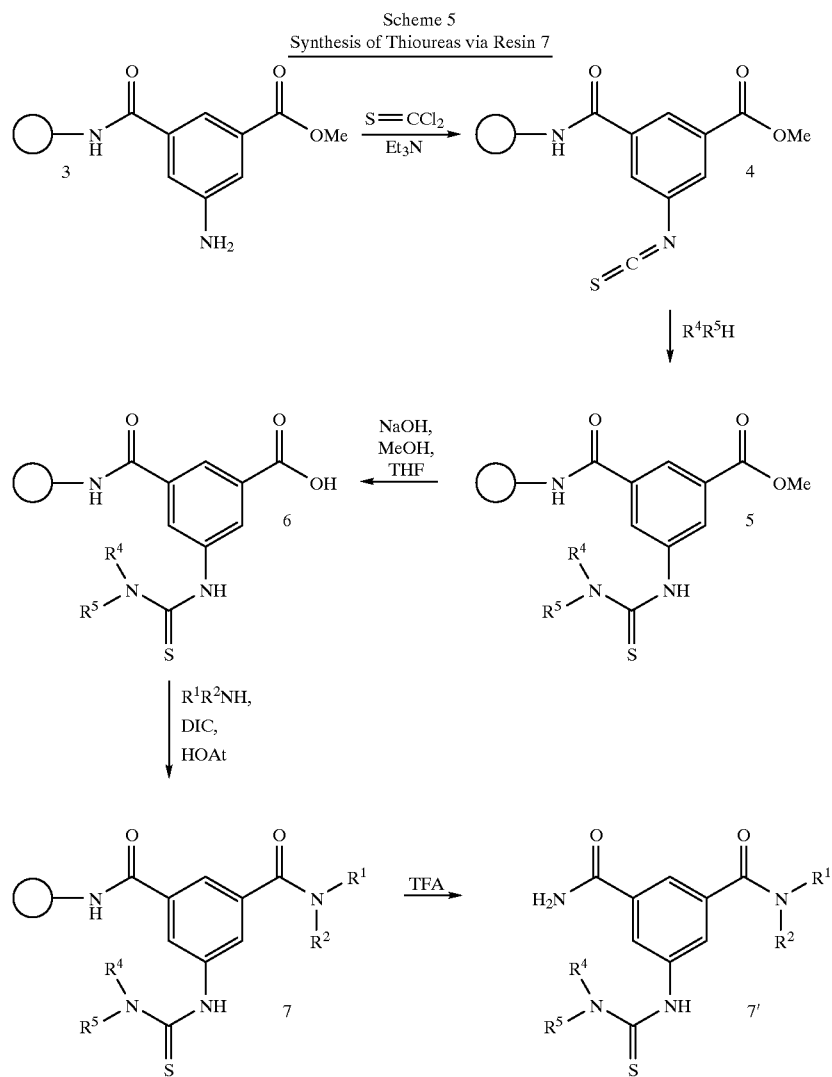

Scheme 5 illustrates the formation of thiourea compounds. Resin 3 was reacted with thiophosgene and triethylamine to give isothiocyanate resin 4. Reaction of resin 4 with a variety of amines gave thiourea resins 5. Hydrolysis of the methyl ester of resins 5 and coupling of resins 6 with a variety of amines via the HOAt/DIC coupling method will provide resins 7. The resulting products can be cleaved from the resin with trifluoroacetic acid (TFA) (Method A, Example 2). If a product contains an electron-rich functional group, such as an indole, the product should be cleaved from the resin with TFA/trialkylsilane (Method B, Example 2).

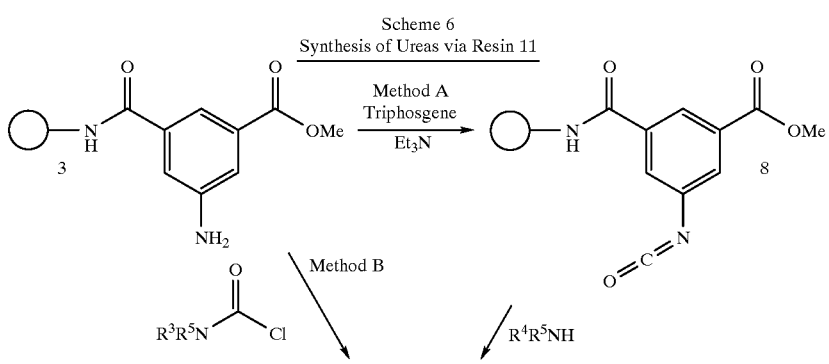

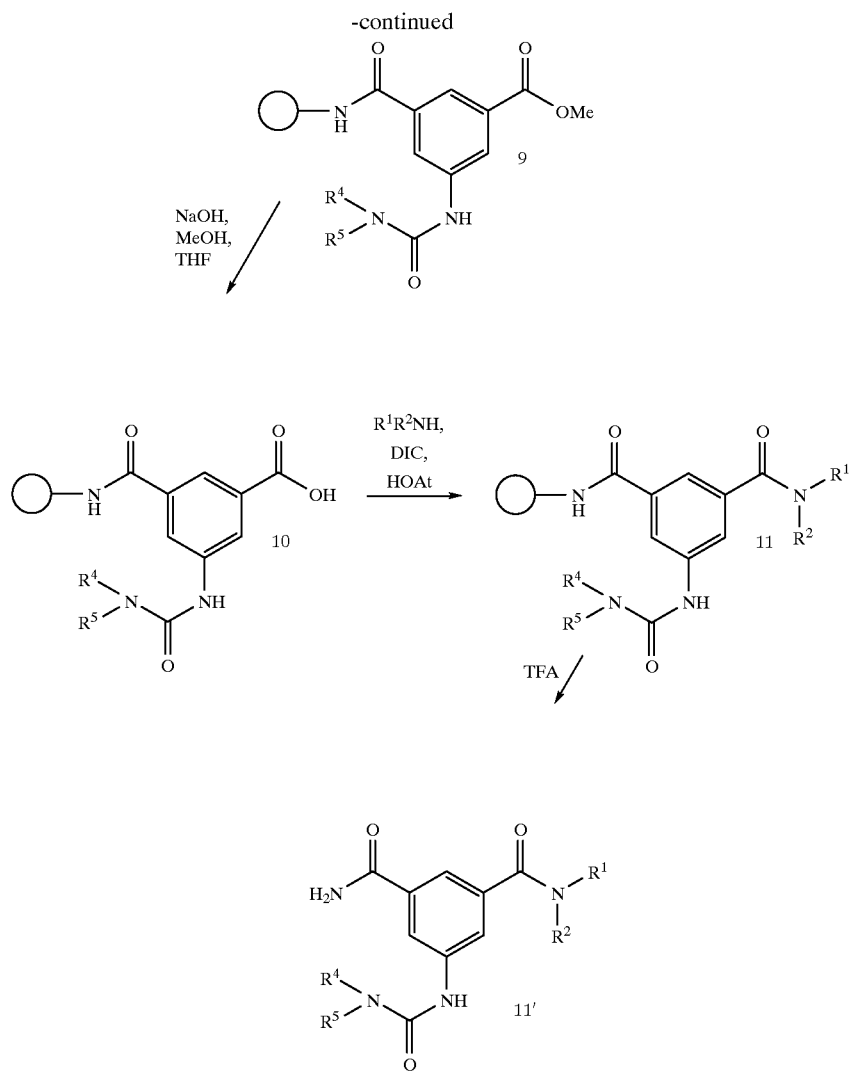

Scheme 6 illustrates the formation of urea compounds. Urea resins 9 were prepared by reacting 3 with triphosgene and triethylamine to give isocyanate resin 8, followed by reaction with appropriate amines (Method A). Alternatively, urea resins 9 can be prepared by reacting resin 3 with carbamoyl chlorides (Method B). Hydrolysis of the methyl ester gave resin 10. Resin 10 was coupled with appropriate amines and clipped with TFA, as above, to give urea products.

Scheme 7
Synthesis of Carbamates via Resin 14

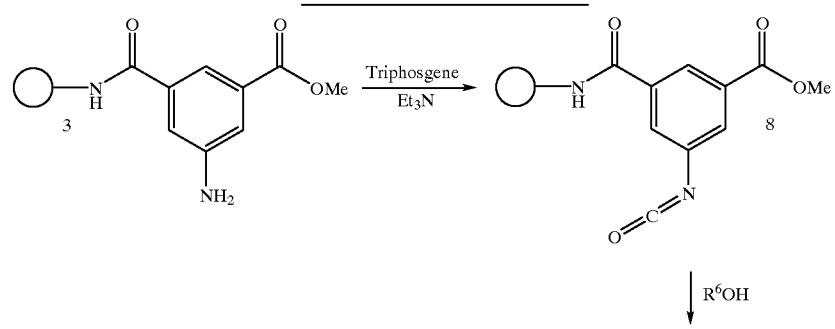

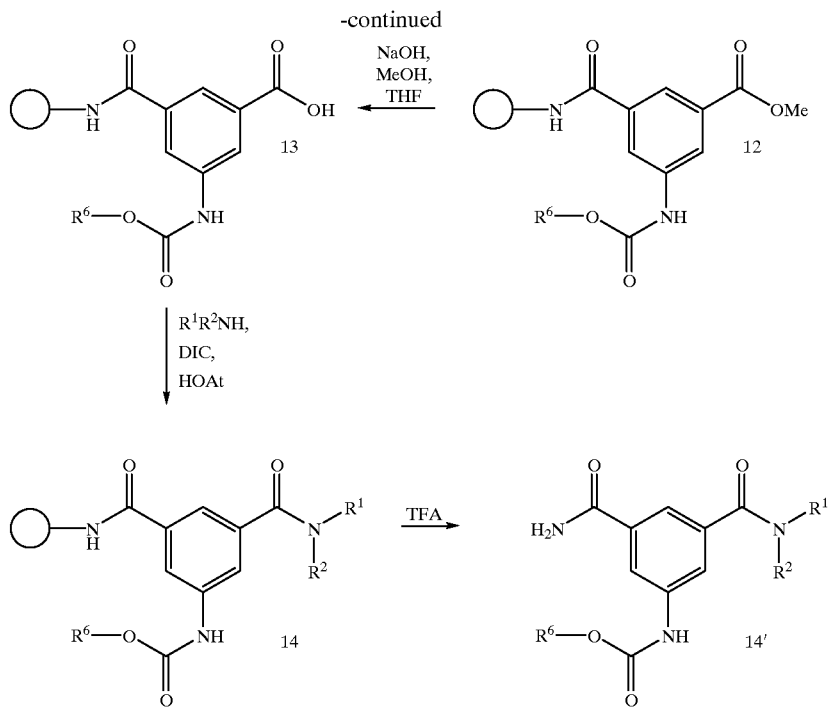
Scheme 7 illustrates the formation of carbamate compounds. Isocyanate resin 8 was reacted with appropriate anhydrous alcohols to give carbamate resin 12. Hydrolysis of the methyl ester gave resin 13. Resin 13 was coupled with appropriate amines and clipped with TFA, as above, to give carbamate products 13'.
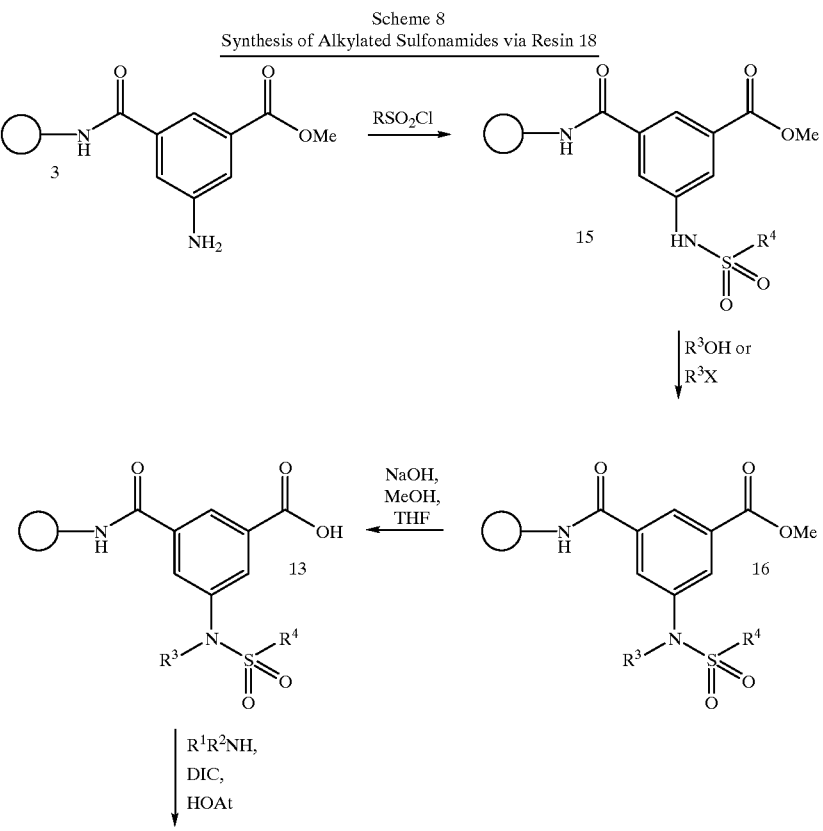

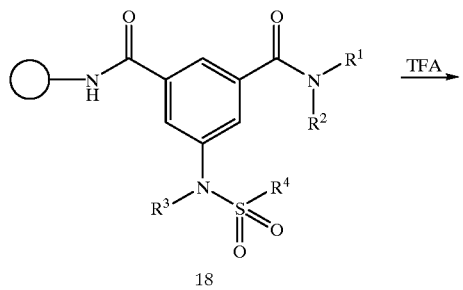
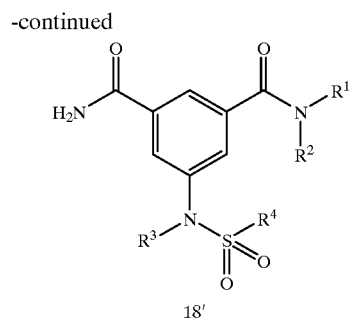

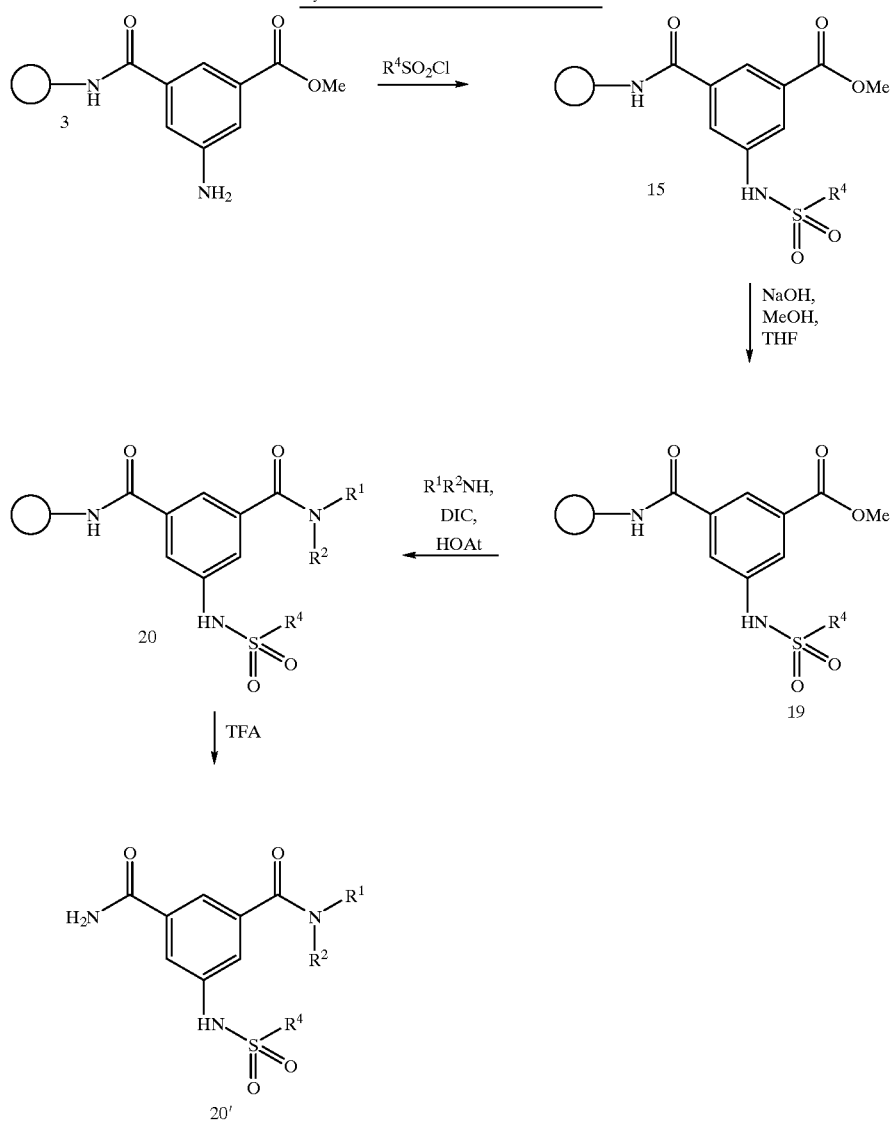

Scheme 8 illustrates the formation of alkylated sulfonamide compounds. Aniline resin 3 was coupled with sulfonyl chlorides to give resins 15. The sulfonamide functional group was alkylated with appropriate alcohols (Methods A and B) or with appropriate alkyl halides (Method C) to give resins 16. Hydrolysis of the methyl ester gave resin 17. Resin 17 was further coupled with appropriate amines and clipped with TFA, as above, to give urea products.

Scheme 9 illustrates the formation of sulfonamide compounds wherein $R^3$ is hydrogen. The procedures described for Scheme 8 are followed except that the alkylation step is omitted.

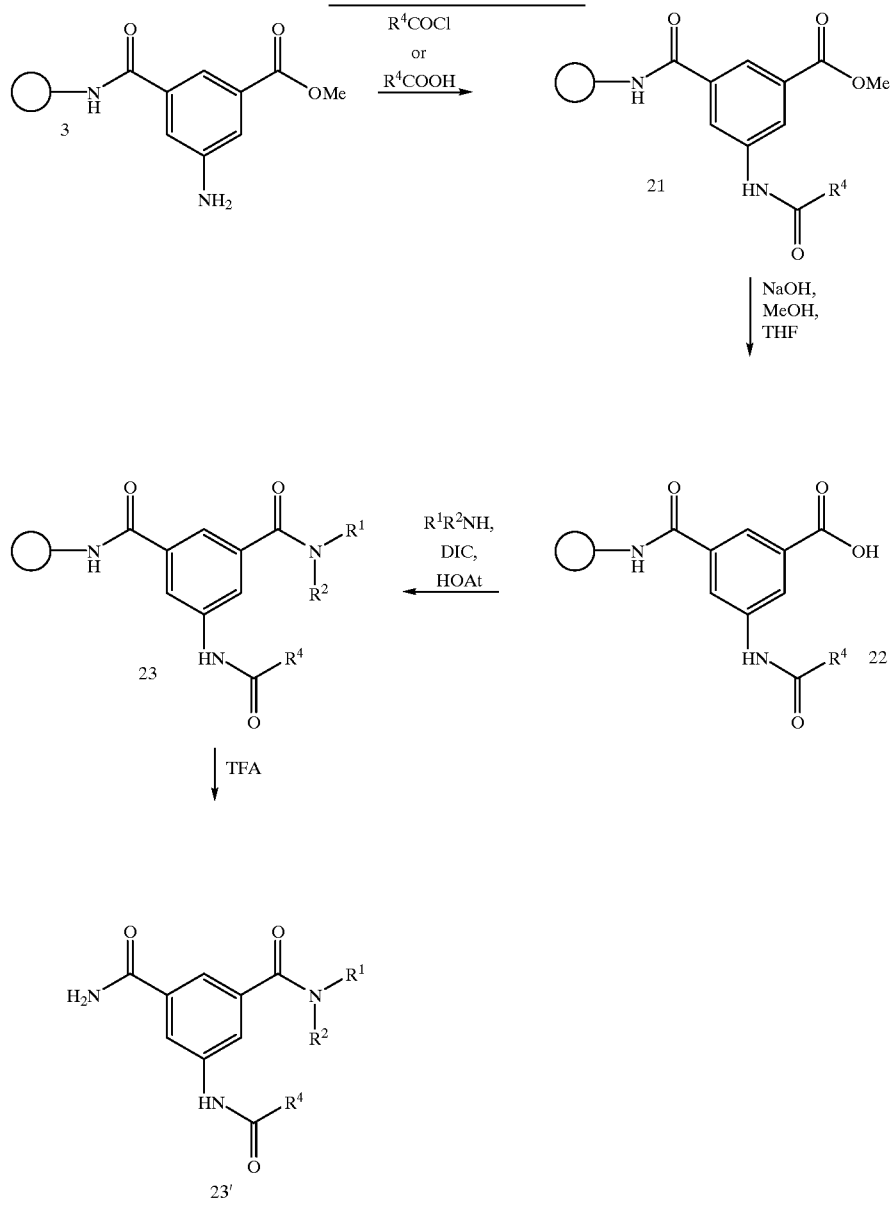
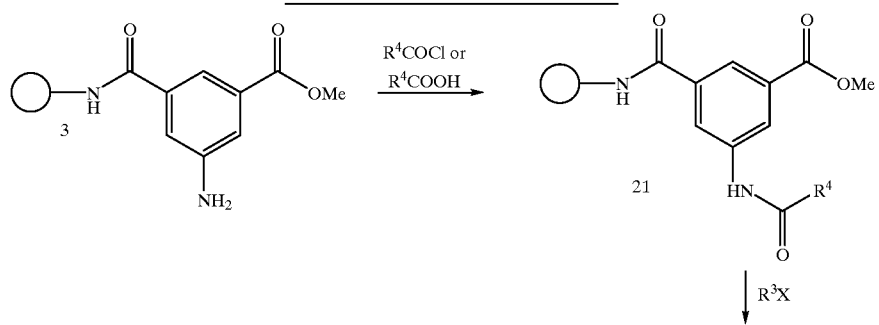

-continued

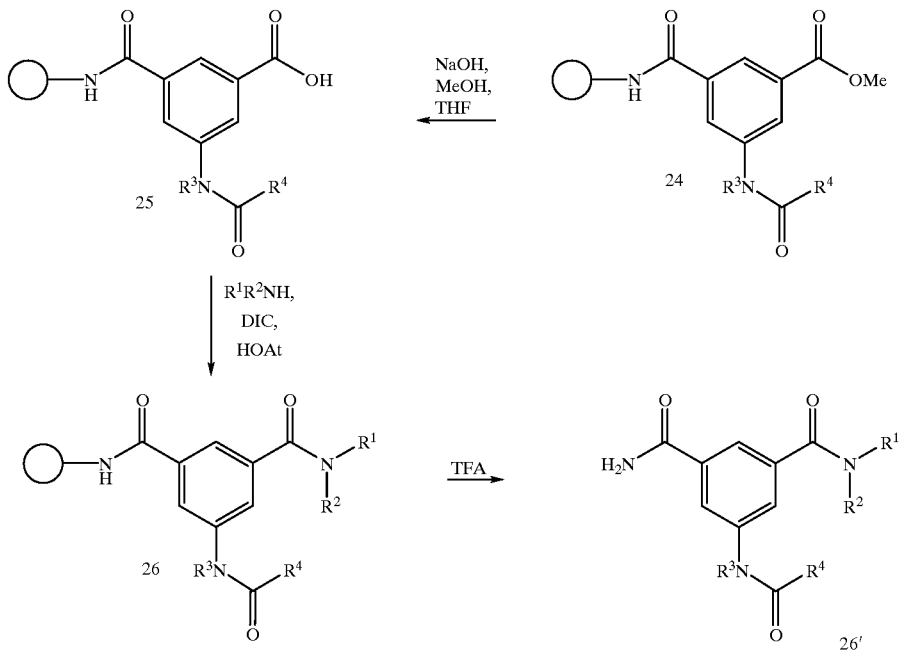

Scheme 10 illustrates the formation of amide compounds. Amide resins 21 were synthesized from aniline resin 3 by coupling it with acid chlorides (Methods A and B) or carboxylic acids (Methods C and D). Hydrolysis of the methyl ester gave resins 22. Resins 22 were further coupled with appropriate amines and clipped with TFA, as above, to give amide products 23'.

Scheme 11 illustrates the formation of alkylated amide resins 26 and products 26'. Amide resins 21 can be alkylated with agents such as methyl iodide using lithiated N-(4-methoxyphenyl)acetamide as base to give amide resins 24. Resins 24 are then hydrolyzed, coupled with appropriate amines, and clipped with TFA, as above, to give alkylated amide products 26'.

Automated Synthesis and Assay of Libraries

A useful computer controlled system for use in synthesizing and/or assaying libraries of the present invention is described in U.S. Pat. No. 5,463,564.

In the examples of the present invention, the chemical building blocks are each reacted with the scaffold structure to form the library defined above. A Chemical Synthesis Robot can be employed to combine alcohol, amine, carbamoyl chloride, chloroformate, sulfonyl chlorides, acid chloride, carboxylic acid reagents with the scaffold using solid phase synthetic chemistry techniques to synthesize a library of compounds for biological screening. A database of commercially available reagents for each of these categories can be stored in the data processing device described below. Of course, the skilled artisan would recognize that a great number of other available reagents can be employed in the methods of the present invention to provide useful libraries. Each compound is generally composed of, but not restricted to an appropriate scaffold (see FIG. 1) and two moieties that have been covalently attached to the scaffold. Thus, the library preferably comprises a plurality of potential protease inhibitors generally composed of, but not restricted to, three sites of variable structure.

In a preferred method of utilizing the library of the present invention, the chemical library generated by a Chemical Synthesis Robot is provided to an analysis robot. The analysis robot analyzes (chemically, biochemically, physically, and/or biophysically) the compounds in the chemical library to obtain structure-activity/structure-property data (called herein Structure-Activity Data) pertaining to the compounds. Such structure-activity/structure-property data includes well known structure-activity/structure property relationship data (collectively referred to as structure-activity relationships or SAR hereafter) pertaining to the relationship(s) between a compound's activity/properties and its chemical structure. Preferably, the analysis robot assays the compounds in the chemical library to obtain enzyme inhibition data. In a similar manner, cellular activity data, toxicology data, and/or bioavailability data pertaining to the compounds can be obtained. Optionally, analysis robot also analyzes the compounds to identify which of the compounds were adequately synthesized, and which of the compounds were not adequately synthesized. This could be useful, since not all combinations of chemical building blocks may interact as expected. The analysis robot further analyzes the compounds to obtain other pertinent data, such as data pertaining to the compounds' composition, structure and electronic structure.

This data obtained by the analysis robot (i.e., physical data, synthesis data, enzyme inhibition data, cellular activity data, toxicology data, bioavailability data, etc.) collectively represents the Structure-Activity Data. The Structure-Activity Data is stored in a Structure-Activity Database.

Preferably, the synthesis and analysis of the libraries of the present invention are controlled by a data processing device, such as a computer operating in accordance with software. Consequently, it is possible to store massive amounts of data, and to utilize this data in a current iteration to generate robotic synthesis instructions for a further iteration of synthesis. In particular, since the elements of the present invention are controlled by a data processing device, it is possible to store the Structure-Activity Data obtained during each iteration. It is also possible to utilize the historical structure-activity data obtained during previous iterations, as well as other pertinent structure-activity data obtained by other experiments, to generate robotic synthesis instructions for a next iteration. In other words, the synthesis of the a library for the next iteration is guided by the results of all previous iterations (or any subset of the previous iterations, as determined by user input, for example) such that the method "learns" from its past performance. As a result, lead compounds identified in subsequent iterations should exhibit physical, chemical and/or biological properties closer to the prescribed values than the leads identified in prior iterations.

According to a preferred embodiment of the present invention, one or more robots (i.e., the Chemical Synthesis Robot) are used to robotically synthesize the chemical library. Also, one or more robots (i.e. the analysis robot) are used to robotically analyze the compounds contained in the library during each iteration. As used herein, the term "robot" refers to any automated device that automatically performs functions specified by instructions, such as the robotic synthesis instructions which the Chemical Synthesis Robot receives from a Synthesis Protocol Generator or are inputted by a user. The integrated use of data processing devices (i.e., the Synthesis Protocol Generator) and robots (i.e., the Chemical Synthesis Robot and the analysis robot) in the present invention enables the automatic and intelligent synthesis and screening of very large numbers of chemical compounds.

The Chemical Synthesis Robot preferably performs parallel microscale synthesis of a specific combinatorial library of compounds. The Chemical Synthesis Robot preferably cleaves and separates the compounds of the library from the solid support material and distributes the compounds into preferably 96 wells with from 1 to 20 library compounds per well, corresponding to an output of 96 to 1920 compounds per synthetic cycle iteration. This function may alternatively be performed by a well known liquid transfer robot. Chemical synthesis robots suitable for use with the present invention are well known and are commercially available.

| Manufacturer | City | State | Model |
|---|---|---|---|
| Advanced Chemtech | Louisville | KY | 357MPS, 496MOS, 384HTS |
| Argonaut Technologies | San Carlos | CA | Nautilus ™ 2400 |
| Bohdan Automation, Inc. | Mundelein | IL | RAM ™ Synthesizer |
| DIVERSOMER Technologies, Inc. | Ann Arbor | MI | DTI2000 Series |
| TECAN U.S. | Research Triangle Park | NC | GENESIS/Combitech |

Any of the above devices are suitable for use with the present invention. The nature and implementation of modifications to these devices (if any) so that they can operate as discussed herein will be apparent to persons skilled in the relevant art. Resins and compounds of the present invention can also be prepared in a non-automated manner if desired.

The following examples are illustrative, but not limiting, of the method and compositions of the present invention. Other suitable modifications and adaptations of the variety of conditions and parameters normally encountered and obvious to those skilled in the art are within the spirit and scope of the invention.

Example 1

Preparation of Resin 3

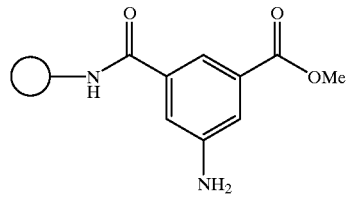

a. Resin 1 (Removal of FMOC Protecting Group): 15.0 g of FMOC-protected Rink amide MBHA resin (0.55 mmol/g, 8.25 mmol, Novabiochem) was pre-swelled with DMF then mixed with 20% piperidine in 1-methyl-2-pyrrolidinone (100 mL) for 5 minutes. Excess solution was drained, and the resin was mixed with fresh 20% piperidine in 1-methyl-2-pyrrolidinone (100 mL) for 20 minutes. Solution was drained and resin 1 was washed with DMF (6×100 mL), methanol (100 mL), dichloromethane (3×100 mL), and methanol (100 mL).

b. Resin 2: A solution of mono-methyl 5-nitroisophthalate (9.3 g, 41 mmol), 1-hydroxy-7-azabenzotriazole (HOAt, 5.6 g, 41 mmol), and 1,3-diisopropylcarbodiimide (DIC, 6.4 mL, 41 mmol) in anhydrous tetrahydrofuran (40 mL) was mixed for 30 min, then it was added to resin 1 (pre-swelled with anhydrous tetrahydrofuran). The resulting mixture was agitated for 20 h. The solution was drained, and was washed multiple times with 25 mL portions of DMF, dichloromethane and t-butyl methyl ether to provide resin 2. A portion of resin 2 can be clipped (trifluoroacetic acid clip, method A) and the product analyzed to determine resin loading. Loading of resin 2 was estimated to be 0.5 mmol/g.

c. Resin 3: Resin 2 was pre-swelled with DMF and mixed with 2.0M tin (II) chloride dihydrate (150 mL, 300 mmol) for 6.5 h. Solution was drained and the resin was washed multiple times with 25 mL portions of DMF, t-butyl methyl ether, 20% N,N-diisopropylethylamine in DMF, and dichloromethane. The resin was dried under vacuum to provide 14.7 g of resin 3. A portion of resin 3 (30 mg) was clipped with trifluoroacetic acid as described in the trifluoroacetic acid clip, Method A, to assure complete conversion to aniline. (See Example 2 for "clip" protocols.)

Example 2

General Protocol for Synthesis of Thiourea Derivatives on Solid Support (7)

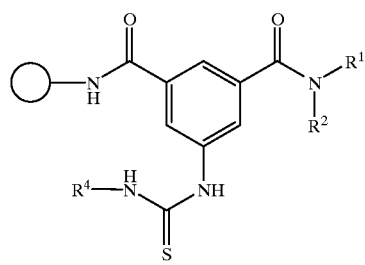

The following general protocol was followed to synthesize molecularly diverse sub-libraries of thiourea compounds. Various amines are selected for reacting with resin 4 in step b, and various amines are selected for reacting with resin 6 in steps d and d'.

a. Resin 4: 10 mL of a thiophosgene solution (0.16M in dichloroethane, 1.6 mmol) was added to a mixture consisting of 500 mg resin 3 (0.5 mmol/g, 0.25 mmol), 5.4 mL dichloroethane, and 400 mL triethylamine (2.75M in dichloroethane, 1.1 mmol). The reaction was mixed for 4 h. Solution was drained and resin 4 was washed with dichloroethane (3×15 mL) and t-butyl methyl ether (10 mL). The resin was dried under vacuum for 1 h then stored under anhydrous conditions until use.

b. Resin 5: 50 mg of resin 4 (0.5 mmol/g, 0.025 mmol) and a solution of an appropriate amine (950 µL, 0.5M in dichloroethane, 0.475 mmol) were mixed for 6 h. The resulting solution was drained and resin 5 was washed multiple times with 2000 µL portions of dichloroethane, DMF and t-butyl methyl ether.

c. Resin 6: 50 mg of resin 5 (0.5 mmol/g, 0.025 mmol), tetrahydrofuran (1000 µL) and 500 µL sodium hydroxide solution (1:3 v/v 3.5N NaOH/methanol) were mixed for 5 h. The solution was drained and the sodium hydroxide hydrolysis step repeated. The resin was acidified by mixing with tetrahydrofuran (825 µL) and methanolic hydrochloric acid (175 µL, 1:1 v/v 10% HCl/methanol) for one minute. The acidification was repeated twice, and then resin 6 was washed multiple times with 1000 µL portions of tetrahydrofuran, methanol and dichloroethane.

d. Resin 7, Method A: 50 mg of resin 6 (0.5 mmol/g, 0.025 mmol) was pre-swelled with anhydrous tetrahydrofuran (1000 µL) for 1 min, then solvent was drained. The carboxylic acid functionality was preactivated by mixing the resin with HOAt (250 µL, 0.6M in 1:1 v/v anhydrous tetrahydrofuran/DMF) and DIC (250 µL, 0.6M in anhyd tetrahydrofuran) for 60 min. The resulting solution was drained and the resin was washed with anhydrous tetrahydrofuran (1000 µL). A solution of an appropriate amine (600 µL, 0.5M for amines and 1M for diamines or amino alcohols in 1:1 v/v methyl sulfoxide/DMF) was added and the reaction was mixed for 14 h. The resulting solution was drained and the resin was washed with anhydrous tetrahydrofuran (2×1000 µL). The preactivation step and tetrahydrofuran washes were repeated, then fresh amine solution (600 µL) was added and the reaction was mixed for 6 h. Solution was drained and the resin was washed multiple times with 1000 µL portions of DMF, methanol and dichloroethane. Resin 7 was dried under high vacuum overnight prior to ligand cleavage by trifluoroacetic acid clip (Method A or B).

d'. Resin 7, Method B: Resin 6 (0.05 g, 0.5 mmol/g, 0.025 mmol) was pre-swelled with tetrahydrofuran (1000 µL) for 1 min, then solvent was drained. A solution of the appropriate amine (800 µL, 0.5M for amines and 1M for diamines or amino alcohols in DMF) was added and the mixture was agitated for 2 min. Benzotriazole-1-yloxy-tris-pyrrolidinophosphonium hexafluorophosphate (PyBOP®) solution (250 µL, 0.6M in DMF) was added. The reaction was mixed for 14 h then drained. The resin was washed multiple times with 1000 µL portions of tetrahydrofuran, DMF, methanol, and dichloroethane. The resin was then dried under high vacuum overnight prior to ligand cleavage by trifluoroacetic acid clip (method A or B) to form thiourea compounds 7'.

e. Trifluoroacetic Acid Clip, Method A: 50 mg of resin (0.5 mmol/g, 0.025 mmol) was mixed with trifluoroacetic acid solution (1000 µL of 1:19:20 v/v/v water/trifluoroacetic acid/dichloroethane) for 1 h. Filtrate was collected, and the resin was washed for 1 minute with trifluoroacetic acid solution (500 µL) and for 1 minute with dichloroethane (500 µL). Filtrates were combined, toluene (500 µL) was added, and the solution was concentrated in vacuo to provide the product.

e'. Trifluoroacetic Acid Clip, Method B: 50 mg of resin (0.5 mmol/g, 0.025 mmol) was mixed with trifluoroacetic acid/ triethylsilane solution (1000 µL of 15:5:80 v/v/v trifluoroacetic acid/ triethylsilane/dichloroethane) for 1 h. Filtrate was collected, and the resin was washed for 1 minute with dichloroethane (500 µL) and for 1 minute with trifluoroacetic acid/triethylsilane solution (500 µL). Filtrates were combined, toluene (500 µL) was added, and the solution was concentrated in vacuo to provide the product.

Example 3

General Protocol for Synthesis of Urea Derivatives on Solid Support (11)

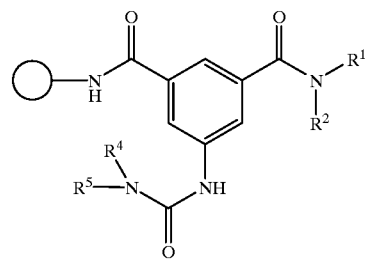

The following protocol was followed to synthesize a molecularly diverse sub-library of urea compounds.

a. Resin 8: Triphosgene solution (163.2 mg in 10 mL dichloroethane, 0.55 mmol) was added over 1 min to a mixture of 500 mg resin 3 (0.5 mmol/g, 0.25 mmol), 4.8 mL dichloroethane and 200 µL triethylamine solution (2.75M in dichloroethane, 0.55 mmol). The reaction was mixed at room temperature for 3 h under nitrogen atmosphere. Excess solution was drained and resin 8 was washed with anhydrous dichloroethane (5×5 µL) and t-butyl methyl ether (3 mL). The resin was dried under vacuum for 30 min before it was used in the next step.

b. Resin 9, Method A: 50 mg of resin 8 (0.5 mmol/g, 0.025 mmol) was treated with a solution of an appropriate amine (700 µL, 0.5M in dichloroethane) and mixed for 6 h under nitrogen atmosphere. Solution was drained and resin 9 was washed multiple times with 1000 µL portions of dichloroethane, DMF, methanol and tetrahydrofuran.

b'. Resin 9, Method B: 50 mg of resin 3 (0.5 mmol/g loading estimated, 0.025 mmol) and dichloroethane solutions of pyridine (200 µL, 1:1 v/v pyridine:dichloroethane) and an appropriate carbarnyl chloride (700 µL, 1M, 0.7 mmol) were treated for 6 h. The resulting solution was drained and the resin was washed with dichloroethane (100 µL). The resin was again treated with dichloroethane solutions of pyridine (200 µL) and carbamoyl chloride (700 µL). After mixing for 12 h, the solution was drained and resin 9 was washed with dichloroethane (2×100 µL), DMF (3×1000 µL), dichloroethane (4×1000 µL), and tetrahydrofuran (1000 µL).

c. Resin 10: Resin 10 was prepared by the same procedure employed for forming resin 6 in Example 2 by substituting 50 mg of resin 9. for resin 5.

d. Resin 11: Resin 11 was prepared by the same procedure employed for forming resin 7 in Example 2 by substituting 50 mg of resin 10 for resin 6. Resin 11 was dried under high vacuum overnight and then the ligand 11' was cleaved from the resin by trifluoracetic acid clip (Method A or B, see Example 2).

The compounds listed in Table 1 were prepared according to this example by employing the appropriate amines to form resins 9 and 11:

TABLE 1
Ureas Prepared According to the Method of Example 3
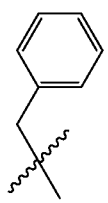
| 3DP | R[1] | R[2] | R[4] | R[5] | Physical Data[a] |
|---|---|---|---|---|---|
| 4166 | 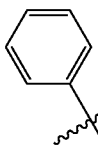 | H | 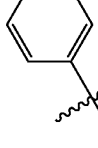 | 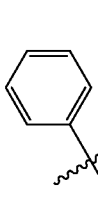 | [M+H]+ calc 465.2; found 465.2 |
| 4186 | 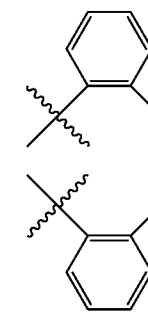 | H |  | | [M+H]+ calc 509.2; found 509.5 |
| 4238 | 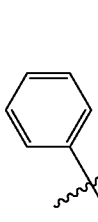 | H | 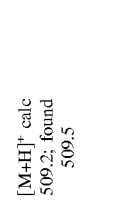 | CH$_3$ | [M+H]+ calc 418.2; found 418.2 |
| 4240 |  | H | CH$_3$ | CH$_3$ | [M+H]+ calc 378.1; found 378.2 |

TABLE 1-continued

Ureas Prepared According to the Method of Example 3

| 3DP | R¹ | R² | R⁴ | R⁵ | Physical Data[a] |
|---|---|---|---|---|---|
| 4247 | piperidinyl-propyl | H | tert-butyl | tert-butyl | [M+H]⁺ calc 390.2; found 390.2 |
| 4249 | isoquinoline-5-sulfonamido-propyl | H | phenyl | (2-(2-ethylphenyl)phenyl) linker | [M+Na]⁺ calc 657.0; found 657.2 |
| 4059 | 4-pyridyl-propyl | CH₃ | benzyl | H | [M+H]⁺ calc 418.5; found 418.4 |
| 4351 | aminopentyl | H | 2-phenylcyclopropyl | H | [M+Na]⁺ calc 418.2; found 418.3 |

TABLE 1-continued
Ureas Prepared According to the Method of Example 3
| 3DP | R[1] | R[2] | R[4] | R[5] | Physical Data[a] |
|---|---|---|---|---|---|
| 4356 | 4-hydroxyphenyl | H | 2-fluorophenyl | H | [M+Na]+ calc 459.1; found 459.1 |
| 4356 | aminoalkyl (NH2(CH2)5) | H | cyclohexyl | H | [M+Na]+ calc 440.3; found 440.2 |
| 4360 | imidazolyl | H | CH3 | H | [M+H]+ calc 331.2; found 331.1 |
| 4361 | 4-aminophenyl | H | benzyl | H | [M+Na]+ calc 440.2; found 440.2 |

TABLE 1-continued
Ureas Prepared According to the Method of Example 3
| 3DP | R[1] | R[2] | R[5] | Physical Data[a] |
|---|---|---|---|---|
| 4390 | 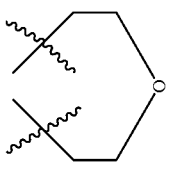 | H | 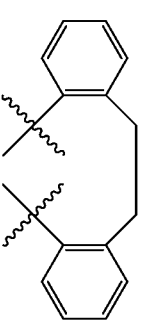 | [M+H]+ calc 378.2; found 378.2 |
| 4250 | 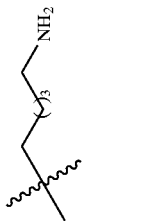 | H | 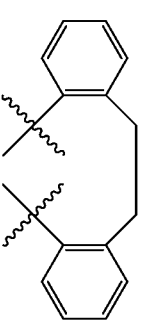 | [M+Na]+ calc 592.2; found 591.9 |
[a]Mass spectral data was collected on KRATOS KOMPACT MALDI III Time of Flight mass spectrometer using α-cyano-4-hydroxycinnamic acid (CHCA) or gentisic acid as matrix.

Example 4

General Protocol for Synthesis of Carbamate Resin on Solid Support 14

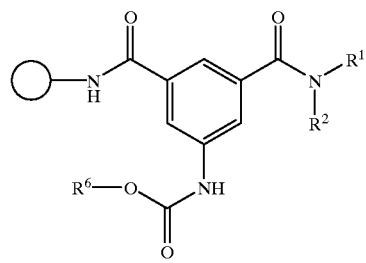

14 a. Resin 8: Resin 8 was prepared as described above in Example 3.

b. Resin 12: 50 mg of resin 8 (0.5 mmol/g, 0.025 mmol) and a solution of the appropriate anhydrous alcohol (700 µL, 1M in dichloroethane) were mixed for 6 h. Solution was drained and the resin was treated with fresh alcohol solution (700 µL). After mixing for 10 h, the solution was drained and resin 12 was washed with dichloroethane (2×1000 µL), methanol (3×1000 µL), dichloroethane (4×1000 µL) and tetrahydrofuran (1000 µL).

c. Resin 13: Resin 13 was prepared by the same procedure employed to form resin 6 in Example 2 by substituting 50 mg of resin 12 for resin 5.

d. Resin 14: Resin 14 was prepared by the same procedures as resin 7 in Example 2, except that 50 mg of resin 13 is substituted for resin 6. Resin 14 was dried under high vacuum overnight and then the ligand 14' was cleaved from the resin by trifluoracetic acid clip (Method A or B, see Example 2).

The compounds listed in Table 2 were prepared according to this example employing the appropriate alcohol and amine starting materials.

TABLE 2

Representative Carbamates Prepared According to the Method of Example 4

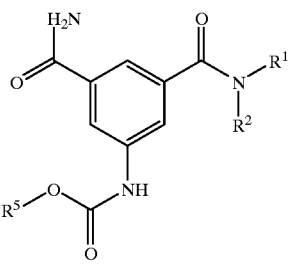

14'

| 3DP | R¹ | R² | R⁶ | Physical Data[a] |
|---|---|---|---|---|
| 4339 | (3-indolylethyl) | H | (pent-4-enyl) | [M+Na]⁺ calc 443.2; found 443.4 |
| 4344 | (cyclopentadienylethyl) | H | (cholesteryl) | [M+Na]⁺ calc 708.4; found 708.9 |
| 4060 | (4-pyridylethyl) | CH₃ | (benzyl) | [M+H]⁺ calc 433.5; found 433.7 |

TABLE 2-continued

Representative Carbamates Prepared According to the Method of Example 4

[structure 14']

| 3DP | R¹ | R² | R⁶ | Physical Data[a] |
|---|---|---|---|---|
| 4353 | [cyclohexane-1,3-diyl-dimethyl] |  | H | [isobutyl] | [M+H]⁺ calc 405.3; found 406.1 |
| 4042 | [n-pentyl] |  | H | [benzyl] | [M+H]⁺ calc 399.5; found 399.1 |

[a]Mass spectral data was collected on KRATOS KOMPACT MALDI III Time of Flight mass spectrometer using α-cyano-4-hydroxycinnamic acid (CHCA) or gentisic acid as matrix.

Example 5

General Protocol for Synthesis of Alkylated Suflonamide Derivatives on Solid Support 18

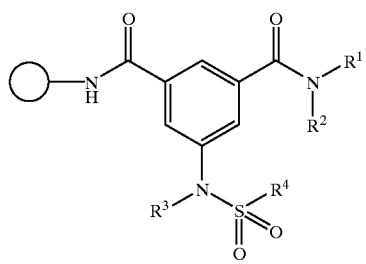

18 a. Resin 15: 50 mg of resin 3 (0.5 mmol/g 0.025 mmol) was pre-swelled with dichloroethane (1000 μL) for 1 min, then solvent was drained. Dichloroethane (300 μL), pyridine (100 μL), and a solution of the appropriate sulfonyl chloride (440 μL, 1M in dichloroethane) were added to the resin, and the reaction was mixed for 6 h. The resulting solution was drained and resin 15 was washed multiple times with 1000 μL portions of dichloroethane, DMF, methanol, and tetrahydrofuran.

b. Resin 16, Method A: The procedure of Krchnak, V. et al., "Polymer Supported Mitsunobu Ether Formation and its Uses in Combinatorial Chemistry," *Tetrahedron Lett.*, 36:6193–6196 (1995) wherein alcohols are coupled with other alcohols was extended to couple alcohols with sulfonamides. 50 mg of resin 15 (0.54 mmol/g, 0.027 mmol) was pre-swelled with 1000 μL anhydrous tetrahydrofuran then treated with 200 μL anhydrous tetrahydrofuran and solutions of 500 μL triphenylphosphine (1M in anhydrous tetrahydrofuran, 0.5 mmol) and an appropriate alcohol (250 μL, 2M in anhydrous tetrahydrofuran, 0.5 mmol). The mixture was shaken for one minute, then diethyl azodicarboxylate (DEAD, 500 μL total, 1M in anhydrous tetrahydrofuran, 0.5 mmol) was added in four 125 μL portions with 10 min mixing between additions. The reaction was mixed for 3.5 h, the solution was drained, and resin 16 was washed multiple times with 1000 μL portions of tetrahydrofuran, dichloroethane, and methanol.

b'. Resin 16, Method B: 50 mg of resin 15 (0.54 mmol/g, 0.027 mmol) was pre-swelled with anhydrous tetrahydrofuran (1000 μL), then treated with anhydrous tetrahydrofuran (250 μL), and solutions of an appropriate alcohol (250 μL, 2M in anhydrous tetrahydrofuran, 0.5 mmol), and tributylphosphine (250 μL, 2M in anhyd tetrahydrofuran, 0.5 mmol). The mixture was shaken for one minute. Thereafter, 1,1'-(azodicarbonyl)dipiperidine (1000 μL total, 0.5M in anhyd tetrahydrofuran, 0.5 mmol) was added in four 250 μL portions with 10 min mixing between additions. (See Tsunoda, T., et al., "1,1'-(Azodicarbonyl) dipiperidine-Tributylphosphine, A New Reagent System for Mitsunobu Reactions," *Tetrahedron Lett.*, 34:1639–1642 (1993)). The reaction was mixed for 3.5 h, then the solution was drained and resin 16 was washed multiple times with 1000 μL portions of tetrahydrofuran, dichloroethane, and methanol.

b". Resin 16, Method C: 50 mg of resin 15 (0.54 mmol/g, 0.027 mmol) was mixed with 1,8-diazabicyclo[5.4.0]undec-7-ene (DBU, 40 μL, 0.27 mmol) in anhydrous DMF (1 mL) for 1 min. A solution of an appropriate alkyl halide (0.54 mmol) was then added. The reaction was mixed for 4.5 h. Resin 16 was filtered and washed multiple times with DMF, dichloromethane and methanol.

c. Resin 17: Resin 17 was prepared by the same procedure used for resin 6 in Example 2, except that 50 mg of resin 16 is substituted for resin 5.

d. Resin 18: Resin 18 was prepared by the same procedure used for resin 7 in Example 2, except that 50 mg of resin 17 is substituted for resin 6.

Example 6

General Protocol for Preparing Sulfonamide Derivatives on Solid Support 20

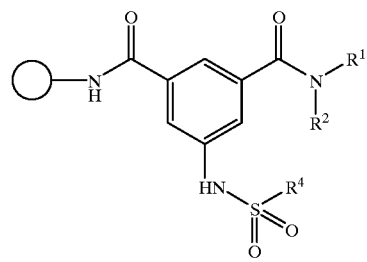

a. Resin 15: Resin 15 was prepared as described above in Example 5.

b. Resin 19: Resin 19 was prepared by the same procedure employed for producing resin 6 in Example 2 except that 50 mg of resin 15 is employed as the starting material.

c. Resin 20: Resin 20 was prepared by the same procedures as resin 7 in Example 2, except that 50 mg of resin 19 is employed in place of resin 6. Sulfonamide compounds 20' were obtained by clipping the ligands using trifluoroacetic acid as described in Example 2. Table 3 lists representative compounds that have been synthesized according to this example by employing the appropriate sulfonyl chlorides and amines.

TABLE 3

Representative Sulfonamides Prepared According to the Method of Example 6

| 3DP | R¹ | R² | R⁴ | Physical Data |
|---|---|---|---|---|
| 4365 | 4-(aminomethyl)benzyl | H | 2-(acetylamino)-4-methylthiazol-5-yl | [M+H]⁺ calc 517.1; found 517.1 |
| 4364 | 4-aminobutyl | H | n-pentyl | [M+H]⁺ calc 371.2; found 371.1 |
| 4194 | 6-(5-(dimethylamino)naphthalen-1-ylsulfonylamino)hexyl | H | 5-(dimethylamino)naphthalen-1-yl | [M+Na]⁺ calc 753.3; found 753.6 |
| 4373 | (4-amino-2-methylpyrimidin-5-yl)methyl | H | 2,4,6-trimethylphenyl | [M+H]⁺ calc 483.2; found 483.0 |

TABLE 3-continued

Representative Sulfonamides Prepared According to the Method of Example 6

| 3DP | R¹ | R² | R⁴ | Physical Data[a] |
|---|---|---|---|---|
| 4409 | (4-(2-morpholinoethyl)methyl) | H | 4-methoxyphenyl | [M+H]⁺ calc 463.2; found 463.1 |
| 4371 | 3-(aminomethyl)benzyl | H | 3,5-dichloro-4-hydroxyphenyl | [M+H]⁺ calc 523.1; found 523.6 |
| 4000 | 2-(pyridin-4-yl)ethyl | CH₃ | phenyl | [M+H]⁺ calc 439.1; found 438.9 |
| 4011 | 3-(1H-imidazol-1-yl)propyl | H | quinolin-8-yl | [M+H]⁺ calc 479.2; found 479.8 |
| 4182 | (4-sulfamoylcyclohexyl)methyl | H | thiophen-2-yl | [M+H]⁺ calc 479.2; found 479.8 |
| 4155 | benzyl | H | CH₃ | [M+H]⁺ calc 334.4; found 334.7 |
| 4658 | 2-(3,4-dihydroxyphenyl)ethyl | H | 2,4,6-trimethylphenyl | [M+Na]⁺ calc 520.2; found 520.1 |

TABLE 3-continued

Representative Sulfonamides Prepared According to
the Method of Example 6

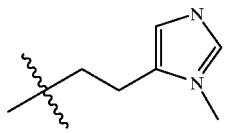

| 3DP | R¹ | R² | R⁴ | Physical Data[a] |
|---|---|---|---|---|
| 4699 |  | H |  | [M+H]⁺ calc 380.1; found 380.1 |

[a] Mass spectral data was collected on KRATOS KOMPACT MALDI III Time of Flight mass spectrometer using α-cyano-4-hydroxycinnamic acid (CHCA) or gentisic acid as matrix.

Example 7

General Protocol for Preparing Amide Derivatives on Solid Support (23)

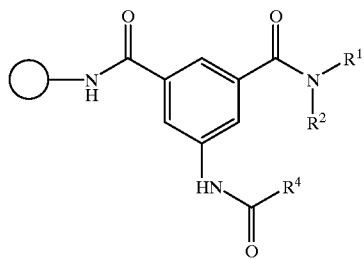

a. Resin 21, Method A: 50 mg of resin 3 (0.5 mmol/g loading estimated, 0.025 mmol) was pre-swelled with dichloroethane (1000 μL) for 1 min, and then solvent was drained. Dichloroethane (300 μL), pyridine (100 μL), and a solution of an appropriate acid chloride (440 μL, 1M in dichloroethane) were added to the resin, and the reaction was mixed for 6 h. The solution was drained and resin 21 was washed multiple times with 1000 μL portions dichloroethane, DMF, methanol, and tetrahydrofuran.

a'. Resin 21, Method B: Oxalyl chloride was sparged with nitrogen, then neat oxalyl chloride (87 μL, 1 mmol) was added to a solution of the appropriate carboxylic acid (2 mL, 0.5M in dichloroethane, 1 mmol). One drop of anhydrous DMF was added to catalyze the reaction. Gas evolution was observed for 15 min. After 45 min of mild agitation, nitrogen was bubbled through the reaction solution for 3 min to remove any excess oxalyl chloride. Additional dichloroethane was added if needed to return the solution to its original volume. The solution, which now contains an acid chloride (0.5M in dichloroethane), w as used as described in the preparation of resin 21, method A.

a". Resin 21, Method C: 50 mg of resin 3 (0.5 mmol/g loading estimated, 0.025 mmol) was pre-swelled with DMF (1000 μL), and then solvent was drained. Solutions of N-[(Dimethylamino)-1H-1,2,3-triazolo[4,5-b]pyridin-1-ylmethylene]-N-methylmethanaminium hexafluorophosphate N-oxide (HATU, 250 μL, 1M in DMF, 0.25 mmol), an appropriate carboxylic acid (250 μL, 1M in DMF, 0.25 mmol), and diisopropylethylamine (250 μL, 2M in 1-methyl-2-pyrrolidinone, 0.5 mmol) were added to the resin and the reaction was mixed for 6 h. The solution was drained and resin 21 was washed multiple times with 1000 μL portions of DMF, dichloroethane, methanol, and tetrahydrofuran.

a'''. Resin 21, Method D: 50 mg of resin 3 (0.5 mmol/g, 0.025 mmol) was pre-swelled with DMF (1000 μL), and then solvent was drained. Solutions of the appropriate carboxylic acid (400 μL, 0.5M in DMF, 0.2 mmol), HOAt (250 μL, 0.6M in DMF, 0.15 mmol), and DIC (250 μL, 0.6M in DMF, 0.15 mmol) were added to the resin, and the reaction was mixed for 6 h. The solution was drained, and the resin was again, if necessary, treated with solutions of carboxylic acid (440 μL), HOAt (250 μL), and DIC (250 μL). After mixing for an additional 10 h, solution was drained and resin 21 was washed multiple times with 1000 μL portions DMF, dichloroethane, and methanol.

b. Resin 22: Resin 22 was prepared by the same procedure as resin 6.

c. Resin 23: Resin 23 was prepared by the same procedure as resin 7 in Example 2, except that 50 mg of resin 22 was employed in place of resin 6. Amide compounds 23' were obtained by trifluoracetic acid clip of resin 23 as described in Example 2. Table 4 lists representative compounds that were synthesized according to this example by employing the appropriate amines and acid chlorides/activated carboxylic acids.

TABLE 4

Representative Amides Prepared According to the Method of Example 7

[Structure: 1,3,5-trisubstituted benzene with H₂N-C(=O)- at position 1, -C(=O)-N(R¹)(R²) at position 3, and -NH-C(=O)-R⁴ at position 5]

23'

| 3DP | R¹ | R² | R⁴ | Physical Data[a] |
|---|---|---|---|---|
| 4133 | -(CH₂)₃-imidazol-1-yl | H | -(CH₂)₂-NH₂ | [M+H]⁺ calc 359.2; found 359.0 |
| 4142 | -(CH₂)₂-(pyridin-4-yl) | CH₃ | 3-cyanophenyl | [M+H]⁺ calc 428.2; found 428.1 |
| 4146 | -(CH₂)₂-phenyl | H | -CH₂-(3-methylphenyl) | [M+H]⁺ calc 416.2; found 416.2 |
| 4168 | phenyl | H | naphthalen-2-yl | [M+H]⁺ calc 410.1; found 410.3 |
| 4201 | -(CH₂)₃-imidazol-1-yl | H | camphor-derived bicyclic lactone | [M+H]⁺ calc 468.2; found 468.3 |
| 4382 | -(CH₂)₂-C(=O)-phenyl | H | 1-adamantyl | [M+Na]⁺ calc 511.2; found 511.4 |
| 4389 | -(CH₂)₅-OH | H | tert-butyl | [M+Na]⁺ calc 372.2; found 372.0 |

TABLE 4-continued

Representative Amides Prepared According to the Method of Example 7

| 3DP | R¹ | R² | R⁴ | Physical Data[a] |
|---|---|---|---|---|
| 4394 | (3,4-dihydroxyphenethyl) | H | (4-tert-butylphenyl) | [M+Na]⁺ calc 498.2; found 498.1 |
| 4395 | (3-hydroxyphenethyl) | H | (cyclopropyl) | [M+H]⁺ calc 368.2; found 368.2 |
| 4423 | (4-morpholinobutyl) | H | (phenoxymethyl) | [M+H]⁺ calc 441.1; found 441.2 |
| 4481 | (4-dimethylaminobenzyl) | H | (benzofuran-2-yl) | [M+Na]⁺ calc 479.2; found 479.4 |
| 4569 | (4-dimethylaminobenzyl) | H | (9-oxofluoren-4-yl) | [M+Na]⁺ calc 541.2; found 541.3 |
| 4579 | (guanidinopentyl) | H | (4-butylphenyl) | [M+H]⁺ calc 453.3; found 453.1 |
| 4593 | (4-(4-methylpiperazin-1-yl)butyl) | H | (cyclohexyl) | [M+H]⁺ calc 430.3; found 430.2 |

TABLE 4-continued

Representative Amides Prepared According to the Method of Example 7

| 3DP | R¹ | R² | R⁴ | Physical Data[a] |
|---|---|---|---|---|
| 4602 | (butyl-piperidine) | H | (thiophene) | [M+H]⁺ calc 401.2; found 401.5 |
| 4603 | (benzyl sulfonamide) | H | (cyclobutyl) | [M+Na]⁺ calc 453.1; found 452.9 |
| 4618 | (4-aminobenzyl) | H | (4-phenoxyphenyl) | [M+Na]⁺ calc 503.2; found 502.9 |
| 4646 | (2-amino-6-methylpyridin-3-ylmethyl) | H | (cyclopentyl) | [M+H]⁺ calc 397.2; found 396.9 |

[a]Mass spectral data was collected on KRATOS KOMPACT MALDI III Time of Flight mass spectrometer using α-cyano-4-hydroxycinnamic acid (CHCA) or gentisic acid as matrix.

Example 8

General Protocol for Preparing Alkylated Amide Derivatives on Solid Support

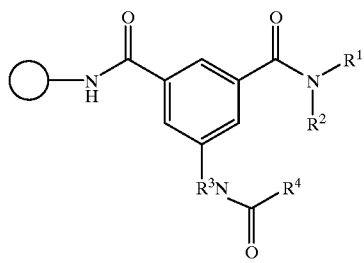

a. Resin 24: Lithiated N-(4-methoxyphenyl)acetamide was prepared as described by Ellman (Boojamra, C. G., et al., *J. Org. Chem.*, 60:5742–5743 (1995)). Lithiated acetamide solution (0.56 mmol estimated, 0.16M in 15:85 v/v DMF/tetrahydrofuran) was added via cannula to 50 mg of resin 21 (0.54 mmol/g, 0.027 mmol) in an oven-dried, nitrogen-flushed flask equipped with septum. The reaction was swirled by orbital mixer for 23 h. Methyl iodide (67 μL, 1.1 mmol) was added and swirling continued for 2.5 days. The resin was filtered and washed multiple times with 1000 μL portions of DMF, dichloromethane and methanol. After drying under vacuum, the resin was clipped with trifluoroacetic acid (Method A) to give 10.0 mg product (95% yield). Alkylhalides, such as methyl iodide, have given clean alkylation reactions under these conditions.

b. Resin 25: Resin 22 can be prepared by the same procedure as resin 6.

c. Resin 26: Resin 26 can be prepared by the same procedure (s) as resin 7.

EXAMPLE 9

General Procedure for Libraries Depicted in FIG. 2 a. Resin 27, Method A: Resin 27 can be prepared by the same procedure employed to convert resin 5 to resin 6.

a'. Resin 27, Method B: Resin 1 (9.34 g, 0.63 mmol/g, 5.9 mmol) was pre-swelled with anhydrous DMF and set aside.

DIC solution (85 mL, 0.35M in DMF, 30 mmol) was added dropwise over 45 minutes to a rapidly stirred solution of 5-nitroisophthalic acid (25.3 g, 120 mmol), HOBt (16.2 g, 120 mmol), and N,N-diisopropylethylamine (41.7 mL, 240 mmol) in anhyd DMF (95 mL) in an oven-dried flask under nitrogen; the reaction was maintained at 22° C. by use of a water bath. The solution was stirred for an additional 30 minutes at room temperature, then it was transferred via cannula to the preswelled resin. The reaction was swirled by orbital mixer for 5 h. Kaiser's test (Kaiser, E., et al., *Anal. Biochem.* 34:595 (1970)) on a few resin beads was negative for free amine. The resin was filtered and washed with 65 mL portions of DMF, 5% water in DMF, dichloromethane and methanol. The resin was dried overnight under vacuum. A portion of the resin was clipped with trifluoroacetic acid, and the isolated product was analyzed to determine loading. Resin loading was 0.54 mmol/g.

b. Resin 28: Resin 28 can be prepared by the same procedure used to convert resin 6 to resin 7, using the same set of amines as can be used to prepare resin 5 from resin 4.

c. Resin 29: Resin 29 can be prepared by the same procedure employed to convert resin 2 to esin 3.

d. Resin 30: Resin 30 can be prepared by the same procedure employed to convert resin 3 to resin 4.

e. Resin 31: Resin 31 can be prepared by the same procedure employed to convert resin 8 to resin 12.

f. Resin 32: Resin 32 can be prepared by the same procedure employed to convert resin 4 to resin 5, using the same set of amines as used to convert resin 6 to resin 7.

g. Resin 33: Resin 33 can be prepared by the same procedure employed to convert resin 3 to resin 8.

h. Resin 34: Resin 34 can be prepared by the same procedure employed to convert resin 8 to resin 9, using the same set of amines as used to convert resin 6 to resin 7.

i. Resin 35: Resin 35 can be prepared by the same procedure employed to convert resin 8 to resin 12.

j. Resin 36: Resin 36 can be prepared by the same procedure employed to convert resin 3 to resin 21.

k. Resin 37: Resin 37 can be prepared by the same procedure employed to convert resin 3 to resin 15.

l. Resin 38: Resin 38 can be prepared by the same procedure employed to convert resin 15 to resin 16.

EXAMPLE 10

General Procedure for Libraries Depicted in FIG. 3 a. Resin 39

Fmoc-protected Rink amide MBHA resin (3.5 g, 0.49 mmol/g, 1.71 mmol, Novabiochem) was preswelled with DMF then mixed with 20% piperidine in DMF (15 mL) for 15 minutes. Excess solution was drained, and the resin was mixed with fresh 20% piperidine in DMF (10 mL) for 15 minutes. Solution was drained and the deprotected resin was washed with DMF (4×20 mL). To this resin was added a solution of 3-hydroxymethyl-5-nitro-benezenecarboxylic acid (0.65 g, 3.29 mmol), 1-hydroxy-7-azabenzotriazole (HOAt, 448.77 mg, 3.32 mmol), HBTU (1.25 g, 3.29 mmol) and N,N-diisopropylethylamine (DIEA, 1.15 mL, 6.61 mmole) in anhydrous DMF (10 mL) and the reaction mixed for 20 h. Solution was drained, and resin was alternately washed with DMF (10 mL) and methanol (10 mL) 3 times, then with THF (10 mL) and methanol (10 mL) 3 times. This resin was then treated with THF (20 mL) and 1:1 v/v 3.5N NaOH: methanol (5 mL) for 8 hr. Thereafter, the solution was drained. Resin 39 was alternately washed with DMF (10 mL) and methanol (10 mL) 3 times, then with dichloroethane (10 mL) and methanol (10 mL) 3 times and dried under vacuum. A portion of resin 39 can be clipped (trifluoroacetic acid clip, method A) and the product analyzed to determine resin loading. Loading of resin was estimated to be 0.49 mmol/g.

b. Resin 40:

Triphosgene (60 mg, 0.2 mmol) in dichloroethane (3 mL) was added to a mixture of resin 39 (200 mg, 0.49 mmol/g, 0.098 mmol), dichloroethane (5 mL) and triethylamine (28 μL, 0.20 mmol). The reaction was mixed at room temperature for 4 h. Excess solution was drained and activated resin was washed with anhydrous dichloroethane (5×5 mL) and t-butyl methyl ether (3 mL). The resin can then be dried under vacuum if desired. The activated resin (50 g, 0.49 mmol/g, 0.0245 mmol) was then treated with a solution of the appropriate amine (700 μL, 0.5M in THF) and mixed for 6 h under nitrogen atmosphere. Solution was drained and resin 40 was alternately washed with DMF (2 mL) and methanol (2 mL) 3 times, then with dichloroethane (2 mL) and methanol (2 mL) 3 times.

c. Resin 41:

Carbon tetrabromide (310.18 mg, 0.93 mmol) in dichloroethane (2 mL) was added to a mixture of resin 39 (0.35 g, 0.49 mmol/g, 0.17 mmol), triphenylphosphine (229.4 mg, 0.85 mmole), and dichloroethane (5 mL). The reaction was mixed for 4 h. Solution was drained and brominated resin was washed with dichloroethane (5×10 mL) and t-butyl methyl ether (8 mL). The resin was dried under vacuum for 10 minutes. The brominated resin (50 mg, 0.49 mmol/g, 0.0245 mmol) and a solution of the appropriate amine (1.4 mL, 0.6M in DMF, 0.84 mmol) were mixed overnight. Solution was drained and resin 41 was alternately washed with DMF (2 mL) and methanol (2 mL) 3 times, then with dichloroethane (2 mL) and methanol (2 mL) 3 times.

EXAMPLE 11

General Procedure for Screening Sub-Libraries for Protease Inhibition Activity

Compounds that are members of the libraries of this invention are screened for biological activity against a number of proteases in the manner described below. Assays are typically performed using a high-throughput screening technique. In the described procedure, 96 well plates, including one or more diverse compounds in each well, are employed.

All buffers and salts are obtained from Sigma Chemical Company (St. Louis, Mo.), and are of the highest purity available. The enzyme substrates, N-benzoyl-Ile-Glu-Gly-Arg-p-nitroanilide hydrochloride (Sigma B2291), N-p-Tosyl-Gly-Pro-Lys-p-nitroanilide (Sigma T6140), and N-CBZ-Val-Gly-Arg-p-nitroanilide (Sigma $C_{7271}$) are obtained from Sigma. N-succinyl-Ala-Ala-Pro-Arg-p-nitroanilide (BACHEM L-1720), N-benzoyl -Phe-Val-Arg-p-nitroanilide (BACHEM L-1150), N-succinyl-Ala-Ala-Pro-Phe-p-nitroanilide (BACHEM L-1400), and N-succinyl-Ala-Ala-Pro-Val-p-nitroanilide (BACHEM L-1770) are obtained from BACHEM (King of Prussia, Pa.).

Human α-thrombin, human factor Xa and human plasmin are obtained from Enzyme Research Laboratories (South Bend, Indiana). Bovine α-chymotrypsin (Sigma $C_{4129}$), bovine trypsin (Sigma T8642) and human kidney cell urokinase (Sigma U5004) are obtained from Sigma. Human leukocyte elastase is obtained from Elastin Products (Pacific, Mo.).

$K_i$ Determinations

All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentration for each of the substrates and each of the enzymes in assay buffer is listed below. Test compounds are prepared in DMSO as 1 mg/ml or 0.16 mg/ml solution. Dilutions are prepared in DMSO yielding 7 final concentrations encompassing a 200-fold concentration range.

In a typical $K_i$ determination, each well of a 96 well plate contains 280 uL of substrate solution, 10 uL of inhibitor solution, and the plate is equilibrated at 37 C. in a Molecular Devices plate reader for >10 minutes. Reactions are initiated by the addition of a 20 uL aliquot of enzyme, and the absorbance increase at 405 nm is recorded for 15 minutes. The ratio of the velocity (rate of the change in absorbance as a function of time) for a sample containing no inhibitor and the velocity of a sample containing inhibitor is plotted as a function of inhibitor concentration. The inverse of the slope of this plot is the experimentally determined $K_i$ value.

Thrombin

Thrombin activity is assessed as the ability to hydrolyze the substrate Suc-Ala-Ala-Pro-Arg-pNA. Substrate solutions are prepared at a concentration of 100 uM in assay buffer. Final DMSO concentration is 4.3%. Purified human α-thrombin is diluted into assay buffer to a final concentration 1.0 nM.

Factor Xa

Factor Xa activity is assessed as the ability to hydrolyze the substrate Bz-Ile-Glu-Gly-Arg-pNA. Substrate solutions are prepared at a concentration of 100 uM in assay buffer. Final DMSO concentration is 4.3%. Purified activated human Factor Xa is diluted into assay buffer to give a final concentration of 2.8 nM.

Plasmin

Plasmin activity is assessed as the ability to hydrolyze the substrate Tos-Gly-Pro-Lys-pNA. Substrate solutions are prepared at a concentration of 100 uM in assay buffer. Final DMSO concentration is 4.3%. Purified human plasmin is diluted into assay buffer to give a final concentration of 2.2 nM.

Chymotrypsin

Chymotrypsin activity is assessed as the ability to hydrolyze the substrate Suc-Ala-Ala-Pro-Phe-pNA. Substrate solutions are prepared at a concentration of 100 uM in assay buffer. Final DMSO concentration is 4.3%. Purified bovine α-chymotrypsin is diluted into assay buffer to give a final concentration of 1.0 nM.

Trypsin

Trypsin activity is assessed as the ability to hydrolyze the substrate Bz-Phe-Val-Arg-pNA. Substrate solutions are prepared at a concentration of 100 uM in assay buffer. Final DMSO concentration is 4.3%. Purified bovine α-chymotrypsin is diluted into assay buffer to a final concentration of 0.9 nM.

Elastase

Elastase activity is assessed as the ability to hydrolyze the substrate N-Succ-Ala-Ala-Pro-Val-p-nitroanilide. Substrate solutions are prepared at a concentration of 100 uM in assay buffer. Final DMSO concentration is 4.3%. Purified human leukocyte elastase is diluted into assay buffer to a final concentration of 6.0 nM.

Urokinase

Urokinase activity is assessed as the ability to hydrolyze N-Cbz-Val-Gly-Arg-p-nitroanilide. Substrate solutions are prepared at a concentration of 100 uM in assay buffer. Final DMSO concentration is 0.3%. Purified human kidney urokinase is diluted into assay buffer to a final concentration of 40 nM.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A composition of matter, comprising a solid support material having a plurality of pendant scaffold moieties covalently attached thereto, wherein said scaffold moieties have the formula:

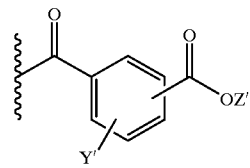

where Y' is nitro;

Z' is hydrogen or a suitable carboxylic acid protecting group; and

⁑ represents the attachment point of the scaffold moiety to the solid support material, wherein said attachment is either directly to the solid support material or via a cleavable linker.

2. The composition of claim 1, wherein; and Z' is trialkylsilyl, alkyl, alkenyl, aryl or aralkyl, any of which is optionally substituted.

3. The composition of claim 1, wherein Z' is methyl.

4. In a solid phase support material useful for the synthesis of organic compounds, wherein said solid phase support originally has a plurality of protected or free pendant amino or hydroxy groups, the improvement comprising one or more scaffold moieties having the formula:

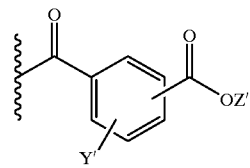

where Y is nitro and Z is hydrogen or a suitable carboxylic acid protecting group; and wherein said scaffold moieties are covalently attached to one or more of said amino or hydroxy groups via an amide or ester linkage.

5. A method for preparing one or more solid support-bound compounds said method comprising the steps of:

(a) attaching a plurality of scaffold structures of the formula:

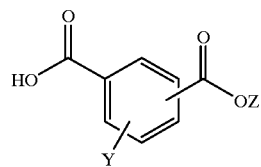

where Y is nitro and Z is a suitable carboxylic acid protecting group to one or more polymeric resin supports by reacting the carboxylic acid functional group of said scaffold with pendant amino or hydroxy groups on said polymeric resin supports to form a plurality of resin-bound scaffolds;

(b) reducing said one or more nitro groups to one or more amino groups;

(c) optionally converting the one or more amino groups at position Y of said resin bound scaffolds to functional groups selected from isocyanato and isothiocyanato;

(d) reacting one or more appropriate organic compounds selected from the group consisting of acid chlorides, sulfonyl chlorides, primary and secondary amines and alcohols, with the amino, isocyanato or isothiocyanato group at position Y on the scaffold molecules whereby the functional group of said one or more organic compounds chemically reacts with the amino, isocyanato or isothiocyanato groups on said scaffold molecules; and (e) hydrolyzing the carboxylic acid ester attached to said one or more resin-bound intermediates and reacting the resulting de-esterified intermediates with at least one primary or secondary amine to form said one or more resin-bound compounds.

6. The method of claim 5, further comprising the step of cleaving said one or more resin bound compounds from said one or more polymeric resins.

\* \* \* \* \*

UNITED STATES PATENT AND TRADEMARK OFFICE
CERTIFICATE OF CORRECTION

| | |
|---|---|
| PATENT NO. | : 6,127,191 |
| APPLICATION NO. | : 08/980062 |
| DATED | : October 3, 2000 |
| INVENTOR(S) | : Todd L. Graybill et al. |

It is certified that error appears in the above-identified patent and that said Letters Patent is hereby corrected as shown below:

Title Page,
Item (56), References Cited, OTHER PUBLICATIONS
"Goff, D.A." reference, please delete "605748-5749." and insert --60:5748-5749 (1995). -- therefor.
"Gordon, E.M." reference, please delete "Discover." and insert -- Discovery. -- therefor.
"Jung, G." reference, please delete "31(4):367383 (1992)." and insert -- 31(4):367-383 (1992). -- therefor.

Column 7,
Line 35, please delete "–$NH_2$" and insert -- –$NH_2$ .-- therefore.

Column 9,
Line 28, please delete "$C_1$ to $C_6$" and insert -- $C_1$ to $C_8$ -- therefor.

Column 10,
Line 39, before "polymeric" insert -- " -- therefor.
Line 45, please delete "cross-inked" and insert -- cross-linked -- therefor.

Column 11,
Line 3, please delete "fised" and insert -- fused -- therefor.

Column 13,
Line 27, please delete "functionalized" and insert -- functionalize -- therefor.

Column 31,
Line 4, after "the" (first occurrence), please delete "a" therefor.

Column 34,
Line 49, please delete "carbarnyl" and insert -- carbamoyl -- therefor.

UNITED STATES PATENT AND TRADEMARK OFFICE
CERTIFICATE OF CORRECTION

PATENT NO. : 6,127,191
APPLICATION NO. : 08/980062
DATED : October 3, 2000
INVENTOR(S) : Todd L. Graybill et al.

It is certified that error appears in the above-identified patent and that said Letters Patent is hereby corrected as shown below:

Columns 35 & 36,
TABLE 1,
Please delete " 14' " and insert -- 11' -- therefor.
Please move "[M+H]$^+$ calc 509.2; found 509.5" to the Physical Data$^a$ column.
Please move "

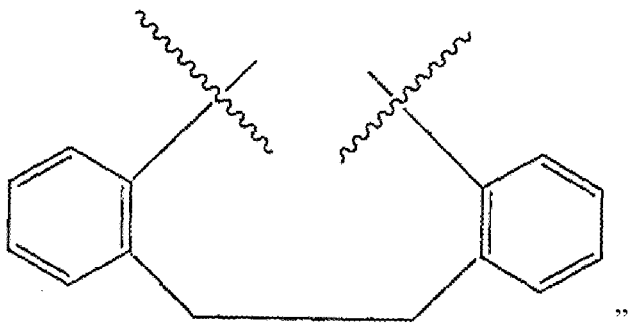

" centered between both columns $R^4$ and $R^5$.

Columns 37 & 38,
TABLE 1 - continued,
Please delete " 14' " and insert -- 11' -- therefor.

Columns 39 & 40,
TABLE 1 - continued,
Please delete " 14' " and insert -- 11' -- therefor.

Columns 41 & 42,
TABLE 1 - continued,
Please delete " 14' " and insert -- 11' -- therefor.

UNITED STATES PATENT AND TRADEMARK OFFICE
CERTIFICATE OF CORRECTION

PATENT NO.        : 6,127,191                      Page 3 of 5
APPLICATION NO.   : 08/980062
DATED             : October 3, 2000
INVENTOR(S)       : Todd L. Graybill et al.

It is certified that error appears in the above-identified patent and that said Letters Patent is hereby corrected as shown below:

Columns 43 & 44,
Table 2,
In the first structure, please delete
" 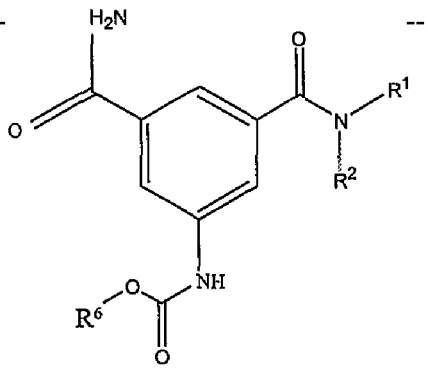 " and insert -- 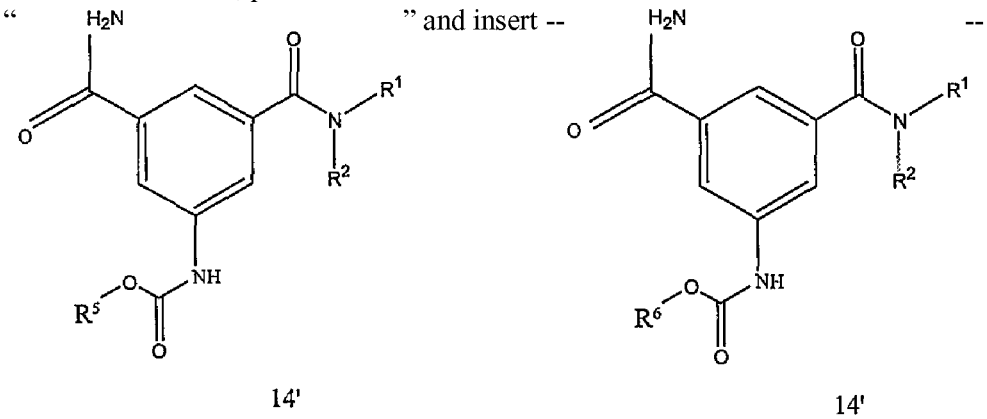 -- therefor.

Columns 45 & 46,
Table 2-continued,
In the first structure, please delete
" 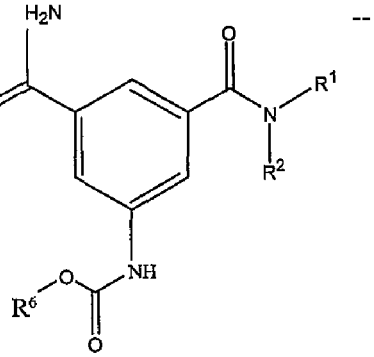 " and insert -- 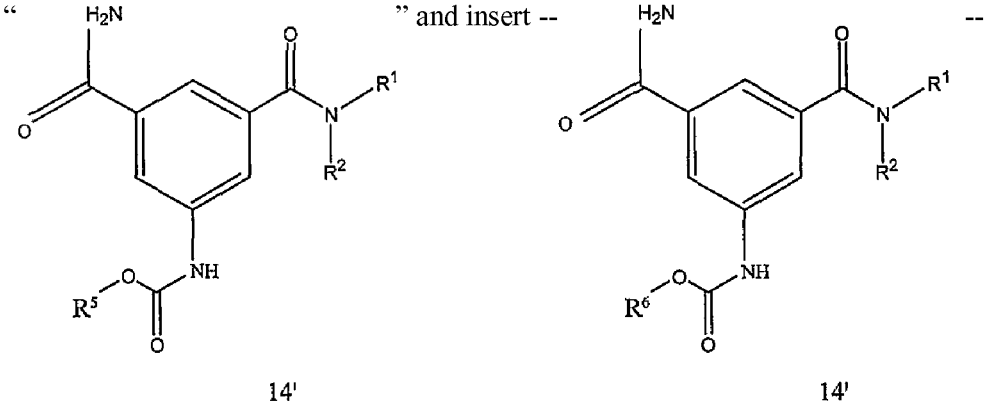 -- therefor.

UNITED STATES PATENT AND TRADEMARK OFFICE
CERTIFICATE OF CORRECTION

PATENT NO. : 6,127,191
APPLICATION NO. : 08/980062
DATED : October 3, 2000
INVENTOR(S) : Todd L. Graybill et al.

It is certified that error appears in the above-identified patent and that said Letters Patent is hereby corrected as shown below:

Columns 45 & 46,
Table 2-continued,
In column $R^1$, line 4353 of the table, please delete
"
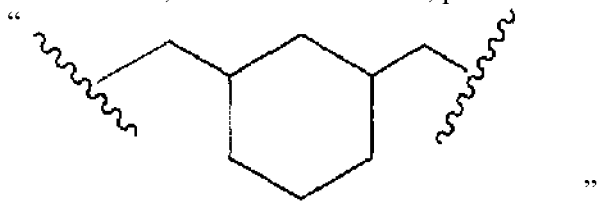
"
and insert
--
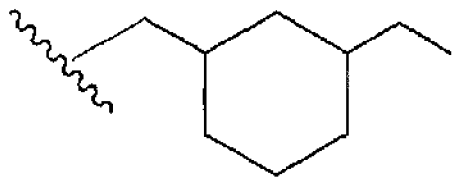
-- therefor.

Column 51,
Line 64, please delete "w as" and insert -- was -- therefor.

Column 52,
Line 29, please delete "N-[(Dimethylamino)-1H-1 ,2,3-triazolo" and insert -- N-[(Dimethulamino)-1H-1,2,3-triazolo -- therefor.

Columns 57 & 58,
Table 4-continued,
In column $R^1$, row 4646 of the table, please delete
" 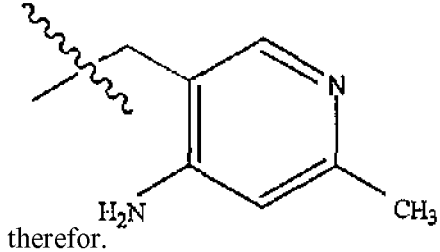 " and insert -- 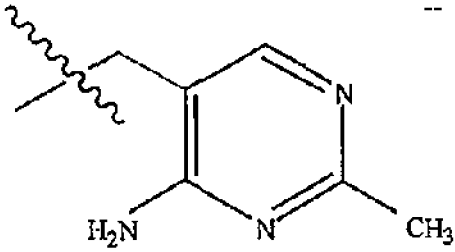 --
therefor.

Column 58,
Line 57, please delete "b.Resin 25: Resin 22" and insert -- b.Resin 25: Resin 25 -- therefor.

UNITED STATES PATENT AND TRADEMARK OFFICE
CERTIFICATE OF CORRECTION

PATENT NO. : 6,127,191
APPLICATION NO. : 08/980062
DATED : October 3, 2000
INVENTOR(S) : Todd L. Graybill et al.

It is certified that error appears in the above-identified patent and that said Letters Patent is hereby corrected as shown below:

<u>Column 59,</u>
Line 22, please delete "esin 3." and insert -- resin 3. -- therefor.

<u>Column 60,</u>
Line 50, please delete "(Sigma $C_{7271}$)" and insert -- (Sigma C7271) -- therefor.
Line 59, please delete "(Sigma $C_{4129}$)," and insert -- (Sigma C4129), -- therefor.

<u>Column 62,</u>
Line 40, please delete "wherein; and Z' is" and insert -- wherein Z' is -- therefor.

Signed and Sealed this

Thirty-first Day of July, 2007

JON W. DUDAS
*Director of the United States Patent and Trademark Office*